(12) United States Patent
Zhao et al.

(10) Patent No.: US 11,654,435 B2
(45) Date of Patent: May 23, 2023

(54) DETECTION CHIP, METHOD FOR OPERATING DETECTION CHIP, AND REACTION SYSTEM

(71) Applicants: BEIJING BOE TECHNOLOGY DEVELOPMENT CO., LTD., Beijing (CN); BOE TECHNOLOGY GROUP CO., LTD., Beijing (CN)

(72) Inventors: Zijian Zhao, Beijing (CN); Siyi Yin, Beijing (CN); Yudan Yin, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 190 days.

(21) Appl. No.: 16/753,115

(22) PCT Filed: Mar. 29, 2019

(86) PCT No.: PCT/CN2019/080626
§ 371 (c)(1),
(2) Date: Apr. 2, 2020

(87) PCT Pub. No.: WO2020/199016
PCT Pub. Date: Oct. 8, 2020

(65) Prior Publication Data
US 2021/0229103 A1 Jul. 29, 2021

(51) Int. Cl.
*B01L 7/00* (2006.01)
*B01L 3/00* (2006.01)
*C12Q 1/686* (2018.01)

(52) U.S. Cl.
CPC .............. *B01L 7/52* (2013.01); *B01L 3/50273* (2013.01); *B01L 3/502715* (2013.01);
(Continued)

(58) Field of Classification Search
None
See application file for complete search history.

(56) References Cited

U.S. PATENT DOCUMENTS

| 2004/0028566 A1 | 2/2004 | Ko et al. |
| 2006/0000709 A1 | 1/2006 | Bohm et al. |

(Continued)

FOREIGN PATENT DOCUMENTS

| CN | 1267089 A | 9/2000 |
| CN | 1460723 A | 12/2003 |

(Continued)

OTHER PUBLICATIONS

First Chinese Office Action from Chinese Patent Application No. 201980000441.2 dated Jul. 30, 2021.

(Continued)

*Primary Examiner* — Xiaoyun R Xu
(74) *Attorney, Agent, or Firm* — Dilworth & Barrese, LLP.; Michael J. Musella, Esq.

(57) ABSTRACT

The detection chip includes a first substrate, a micro-cavity defining layer, a hydrophilic layer, and a hydrophobic layer. The micro-cavity defining layer is on the first substrate and defines a plurality of micro-reaction chambers. Each of the plurality of micro-reaction chambers includes a reaction trap, and the reaction trap includes a sidewall and a bottom. The micro-cavity defining layer includes a spacing region between the plurality of micro-reaction chambers, and the spacing region includes a first region adjacent to the sidewall, and a second region non-adjacent to the sidewall. The hydrophilic layer covers the sidewall and the bottom of each of the plurality of micro-reaction chambers, and the hydrophobic layer covers the second region.

19 Claims, 9 Drawing Sheets

Detection Chip 100

First Substrate 10

Micro-cavity Defining Layer 11

Micro-reaction Chamber 110

Hydrophilic Layer 14

Hydrophobic Layer 13

(52) U.S. Cl.
CPC .......... *C12Q 1/686* (2013.01); *B01L 2300/08* (2013.01); *B01L 2300/165* (2013.01); *B01L 2300/1805* (2013.01); *B01L 2400/088* (2013.01)

(56) References Cited

U.S. PATENT DOCUMENTS

| | | | |
|---|---|---|---|
| 2012/0100551 A1 | 4/2012 | Kojima et al. | |
| 2012/0303449 A1 | 12/2012 | Yang et al. | |
| 2017/0368526 A1 | 12/2017 | Choi et al. | |
| 2018/0126381 A1* | 5/2018 | Huff | B01L 3/502784 |

FOREIGN PATENT DOCUMENTS

| | | |
|---|---|---|
| CN | 1715930 A | 1/2006 |
| CN | 1922478 A | 2/2007 |
| CN | 201732093 U | 2/2011 |
| CN | 102071136 A | 5/2011 |
| CN | 102899245 A | 1/2013 |
| CN | 104588137 A | 5/2015 |
| CN | 105861293 A | 8/2016 |
| CN | 106222068 A | 12/2016 |
| CN | 106501520 A | 3/2017 |
| CN | 107475074 A | 12/2017 |
| CN | 107983426 A | 5/2018 |
| CN | 108660068 A | 10/2018 |
| CN | 108816300 A | 11/2018 |
| CN | 109234158 A | 1/2019 |
| CN | 109289949 A | 2/2019 |
| CN | 209974747 U | 1/2020 |
| KR | 1020140067421 A | 6/2014 |
| KR | 101443074 | 9/2014 |
| WO | 2017/127570 A1 | 7/2017 |
| WO | 2018/183723 A1 | 10/2018 |

OTHER PUBLICATIONS

First Chinese Search Report dated Apr. 1, 2019.
U.S. Office Action from U.S. Appl. No. 16/634,309 dated Jan. 24, 2022.
First Chinese Office Action from Chinese Patent Application No. 201980000439.5 dated Mar. 14, 2022.
Extended European Search Report from Application No. 19858704.0 dated Sep. 9, 2022.
Extended European Search Report from European Patent Application No. 19861273.1 dated Nov. 28, 2022.

* cited by examiner

DETECTION CHIP, METHOD FOR OPERATING DETECTION CHIP, AND REACTION SYSTEM

TECHNICAL FIELD

Embodiments of the present disclosure relate to a detection chip, a method for operating a detection chip, and a reaction system.

BACKGROUND

The polymerase chain reaction (PCR) is a molecular biology technology used for amplifying specific DNA fragments, and the PCR can copy a large amount of deoxyribonucleic acid (DNA) and greatly increase the amount of DNA. Different from traditional PCR technology, digital polymerase chain reaction (dPCR) chip technology can implement the absolute quantitative detection of single molecule DNA by sufficiently diluting the nucleic acid sample to allow the number of target molecules (i.e., DNA templates) in each reaction unit to be less than or equal to one, performing PCR amplification on the target molecules in each reaction unit, respectively, and then statistically analyzing the fluorescent signal of each reaction unit after the amplification. Because the dPCR has advantages of high sensitivity, strong specificity, high detection throughput, accurate quantification, etc., the dPCR is widely used in the fields of clinical diagnosis, gene instability analysis, single-cell gene expression, environmental microorganism detection, prenatal diagnosis, etc.

SUMMARY

At least some embodiments of the present disclosure provide a detection chip, and the detection chip includes: a first substrate; a micro-cavity defining layer on the first substrate and defining a plurality of micro-reaction chambers, in which each of the plurality of micro-reaction chambers includes a reaction trap, the reaction trap includes a sidewall and a bottom, the micro-cavity defining layer includes a spacing region between the plurality of micro-reaction chambers, and the spacing region includes a first region adjacent to sidewalls of the plurality of micro-reaction chambers, and a second region non-adjacent to the sidewalls of the plurality of micro-reaction chambers; a hydrophilic layer covering the sidewall and the bottom of each of the plurality of micro-reaction chambers; and a hydrophobic layer covering the second region in the spacing region of the micro-cavity defining layer.

For example, in the detection chip provided by some embodiments of the present disclosure, the hydrophilic layer further covers the first region in the spacing region of the micro-cavity defining layer.

For example, in the detection chip provided by some embodiments of the present disclosure, the first region is in a circular ring shape, and a width of the circular ring shape is 2 μm to 5 μm.

For example, the detection chip provided by some embodiments of the present disclosure further includes a heating electrode; and the heating electrode is on the first substrate and closer to the first substrate than the micro-cavity defining layer, and is configured to heat the plurality of micro-reaction chambers, and orthographic projections of the plurality of micro-reaction chambers on the first substrate are within an orthographic projection of the heating electrode on the first substrate.

For example, in the detection chip provided by some embodiments of the present disclosure, the plurality of micro-reaction chambers are arranged in an array on the first substrate.

For example, the detection chip provided by some embodiments of the present disclosure further includes a second substrate; and the second substrate is opposite to the first substrate, the hydrophobic layer further covers a side, facing the first substrate, of the second substrate, and the micro-cavity defining layer is on a side, facing the second substrate, of the first substrate.

For example, the detection chip provided by some embodiments of the present disclosure further includes a control electrode; and the control electrode is on the first substrate and is electrically connected to the heating electrode through a via hole or overlapped with the heating electrode, and the control electrode is configured to apply an electrical signal to the heating electrode.

For example, the detection chip provided by some embodiments of the present disclosure further includes a first insulating layer; the first insulating layer covers the control electrode, and the heating electrode is on the first insulating layer; and the first insulating layer includes the via hole penetrating the first insulating layer, and the heating electrode is electrically connected to the control electrode through the via hole.

For example, the detection chip provided by some embodiments of the present disclosure further includes a second insulating layer, and the second insulating layer is between the heating electrode and the micro-cavity defining layer.

For example, in the detection chip provided by some embodiments of the present disclosure, the first substrate includes a reaction region and a peripheral region, the peripheral region is at least partially around the reaction region, the reaction region includes a functional region, the micro-cavity defining layer is in the functional region, the control electrode and the via hole are in the peripheral region, and the heating electrode is in the reaction region and the peripheral region.

For example, in the detection chip provided by some embodiments of the present disclosure, the via hole includes a first via hole group and a second via hole group, and the first via hole group and the second via hole group are on two opposite sides of the peripheral region, respectively; the control electrode includes a first control electrode group and a second control electrode group; the first control electrode group is on a same side as the first via hole group in the peripheral region, and is electrically connected to the heating electrode through the first via hole group; and the second control electrode group extends along the peripheral region and is partially around the heating electrode, and the second control electrode group is electrically connected to the heating electrode through the second via hole group.

For example, the detection chip provided by some embodiments of the present disclosure further includes a plurality of spacers; and the plurality of spacers are in the peripheral region and between the first substrate and the second substrate, and the plurality of spacers are configured to maintain a distance between the first substrate and the second substrate.

For example, in the detection chip provided by some embodiments of the present disclosure, a height of the spacers is greater than a height of the micro-cavity defining layer in a direction perpendicular to the first substrate.

For example, the detection chip provided by some embodiments of the present disclosure further includes a sample inlet and a sample outlet; and the reaction region further includes a non-functional region, the sample inlet and the sample outlet are both in the non-functional region and on different sides of the functional region, and both the sample inlet and the sample outlet penetrate the second substrate and the hydrophobic layer covering the second substrate.

For example, in the detection chip provided by some embodiments of the present disclosure, the sample inlet and the sample outlet are in the non-functional region and are symmetrically distributed on different sides of the functional region.

For example, in the detection chip provided by some embodiments of the present disclosure, both the first substrate and the second substrate are glass substrates.

For example, in the detection chip provided by some embodiments of the present disclosure, a material of the hydrophilic layer includes silicon oxide, and a material of the hydrophobic layer includes resin or silicon nitride.

For example, in the detection chip provided by some embodiments of the present disclosure, a material of the micro-cavity defining layer includes a photoresist.

For example, in the detection chip provided by some embodiments of the present disclosure, a shape of each of the plurality of micro-reaction chambers is a cylinder, a diameter of a bottom surface of the cylinder ranges from 1 μm to 100 μm, and a height of the cylinder ranges from 5 μm to 100 μm.

For example, the detection chip provided by some embodiments of the present disclosure further includes a first temperature sensor; and the first temperature sensor is on a side, away from the micro-cavity defining layer, of the first substrate, and the first temperature sensor is in the reaction region and configured to detect a temperature of the reaction region.

At least some embodiments of the present disclosure further provide a reaction system, and the reaction system includes a control device and the detection chip according to any one of the embodiments of the present disclosure, and the control device is electrically connected to the detection chip, and is configured to apply an electrical signal to the detection chip to drive a heating electrode of the detection chip.

For example, the reaction system provided by some embodiments of the present disclosure further includes a second temperature sensor; and the second temperature sensor is on a side, away from the micro-cavity defining layer, of the first substrate of the detection chip, the second temperature sensor is in a reaction region of the first substrate, and the second temperature sensor is configured to detect a temperature of the reaction region of the detection chip.

At least some embodiments of the present disclosure further provide a method for operating the detection chip according to any one of the embodiments of the present disclosure, and the method includes: allowing a reaction system liquid to enter the plurality of micro-reaction chambers of the detection chip through a sample inlet of the detection chip; and applying an electrical signal to a control electrode of the detection chip, so as to drive a heating electrode of the detection chip to heat the plurality of micro-reaction chambers through the control electrode.

For example, the method provided by some embodiments of the present disclosure further includes: cooling the plurality of micro-reaction chambers to allow temperatures of the plurality of micro-reaction chambers to change, so that the reaction system liquid in the plurality of micro-reaction chambers is subjected to a temperature cycle including a denaturation phase, an annealing phase, and an extending phase.

For example, the method provided by some embodiments of the present disclosure further includes: performing an optical detection on the detection chip to obtain a fluorescent image.

BRIEF DESCRIPTION OF THE DRAWINGS

In order to clearly illustrate the technical solution of the embodiments of the present disclosure, the drawings of the embodiments will be briefly described in the following. It is obvious that the described drawings in the following are only related to some embodiments of the present disclosure and thus are not limitative of the present disclosure.

DETAILED DESCRIPTION

Figure 1:
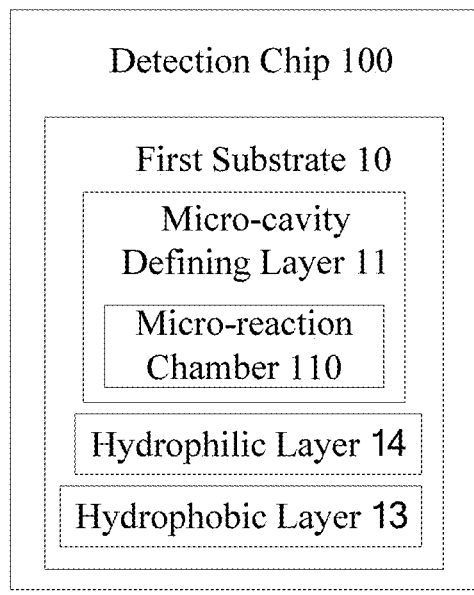
FIG. 1 is a schematic block diagram of a detection chip provided by some embodiments of the present disclosure.

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

Unless otherwise defined, all the technical and scientific terms used herein have the same meanings as commonly understood by one of ordinary skill in the art to which the present disclosure belongs. The terms "first," "second," etc., which are used in the description and the claims of the present application for disclosure, are not intended to indicate any sequence, amount or importance, but distinguish various components. Also, the terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", "coupled", etc., are not intended to define a physical connection or mechanical connection, but may include an electrical connection, directly or indirectly. "On," "under," "right," "left" and the like are only used to indicate relative position relationship, and when the position of the object which is described is changed, the relative position relationship may be changed accordingly.

When the PCR is performed, the double-stranded structure of the DNA fragment is subjected to the denaturation to form the single-stranded structure at a high temperature, primers and single strands are combined according to the principle of complementary base pairing at a low temperature, and base combining extension is implemented at the optimal temperature of the DNA polymerase. The above process is the temperature cycling process of denaturation-annealing-extending. The DNA fragment can implement mass replication through a plurality of temperature cycling processes of denaturation-annealing-extending.

In order to implement the above temperature cycling process, a droplet preparation system is usually required to allow the reaction system liquid to enter the detection chip, and a series of external equipments are used to heat and cool the detection chip, so that the volume of the equipment is large, the operation is complicated, and the cost is high. In addition, during the process of heating and cooling the detection chip, the overall temperature of the detection chip changes accordingly, so that temperatures of other structures and components in the detection chip except for the micro-cavity containing the DNA fragment also change accordingly, thereby increasing risk of damage to components such as circuits. Generally, most dPCR products use silicon-based processing and need to cooperate with the droplet preparation system, so that the cost of the detection chip is high, and the processing is complicated.

At least one embodiment of the present disclosure provides a detection chip, a method for operating a detection chip, and a reaction system. The detection chip facilitates allowing the droplet to automatically enter each micro-reaction chamber, which can implement effective sample injection and avoid liquid interference, and further can effectively implement the temperature control of the micro-reaction chambers of the detection chip, so that the temperature cycle can be implemented without performing the driving operation on the droplet or providing external heating equipment. Therefore, the integration of the detection chip is high, the operation is simple, and the production cost is low.

Hereinafter, the embodiments of the present disclosure are described in detail with reference to the accompanying drawings. It should be noted that the same reference numerals in different drawings are used to refer to the same described components or elements.

At least one embodiment of the present disclosure provides a detection chip, and the detection chip includes a first substrate, a micro-cavity defining layer, a hydrophilic layer, and a hydrophobic layer. The micro-cavity defining layer is on the first substrate and defines a plurality of micro-reaction chambers. Each of the plurality of micro-reaction chambers includes a reaction trap, and the reaction trap includes a sidewall and a bottom. The micro-cavity defining layer includes a spacing region between the plurality of micro-reaction chambers, and the spacing region includes a first region adjacent to sidewalls of the plurality of micro-reaction chambers, and a second region non-adjacent to the sidewalls of the plurality of micro-reaction chambers. The hydrophilic layer covers the sidewall and the bottom of each of the plurality of micro-reaction chambers, and the hydrophobic layer covers the second region in the spacing region of the micro-cavity defining layer.

Figure 2:
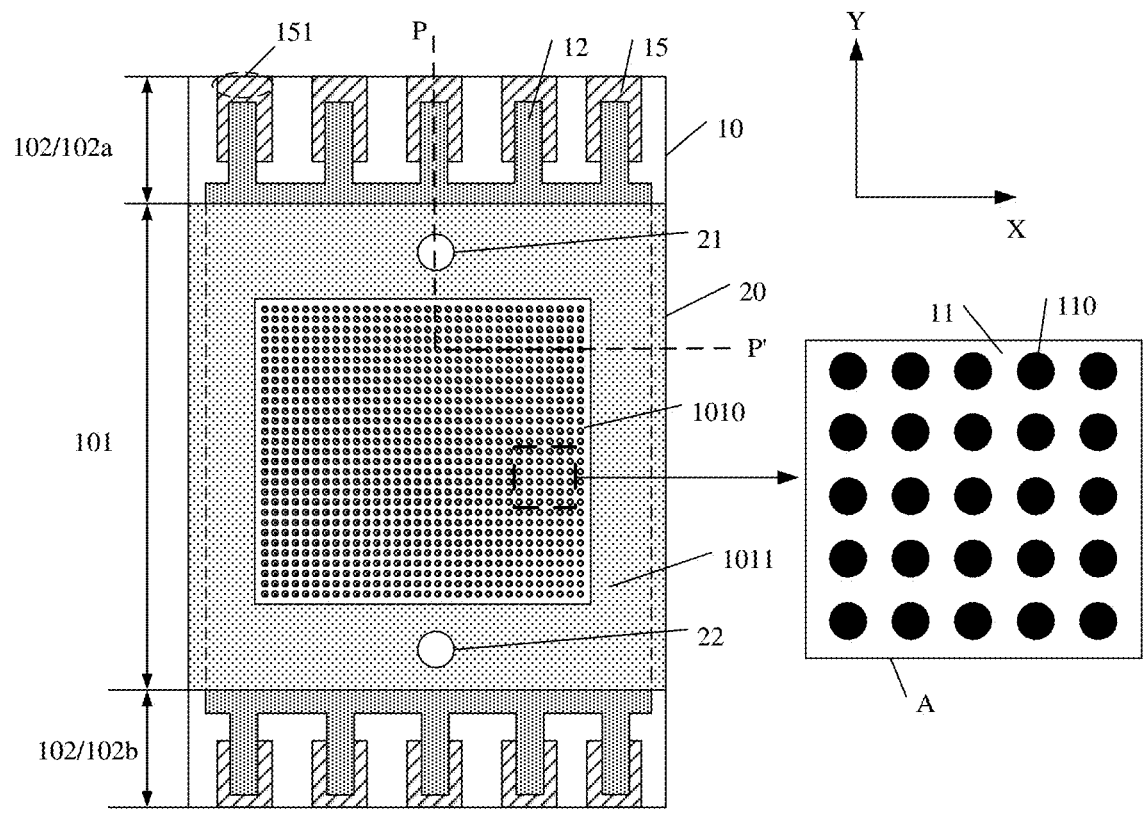
FIG. 2 is a schematic planar diagram of a detection chip provided by some embodiments of the present disclosure.
Figure 3:
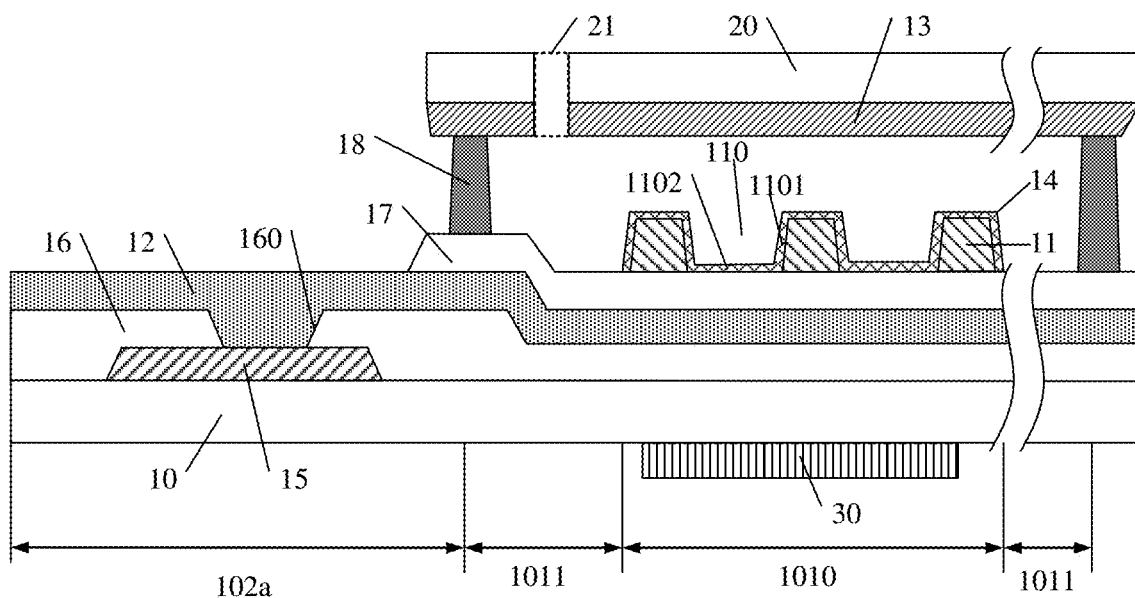
FIG. 3 is a schematic partial cross-sectional structural diagram of a detection chip provided by some embodiments of the present disclosure.

FIG. 1 is a schematic block diagram of a detection chip provided by some embodiments of the present disclosure, FIG. 2 is a schematic planar diagram of a detection chip provided by some embodiments of the present disclosure, and FIG. 3 is a schematic partial cross-sectional structural diagram of a detection chip provided by some embodiments of the present disclosure. For example, FIG. 3 is a cross-sectional view taken along a line P-P' in FIG. 2.

For example, as illustrated in FIG. 1, a detection chip 100 includes a first substrate 10, a micro-cavity defining layer 11, and a heating electrode 12. The first substrate 10 plays a role in protection, supporting, etc. The micro-cavity defining layer 11 and the heating electrode 12 are both located on the first substrate 10. The micro-cavity defining layer 11 defines a plurality of micro-reaction chambers 110. The heating electrode 12 is closer to the first substrate 10 than the micro-cavity defining layer 11 and is configured to heat the plurality of micro-reaction chambers 110. Orthographic projections of the plurality of micro-reaction chambers 110 on the first substrate 10 are located within an orthographic projection of the heating electrode 12 on the first substrate 10. For example, the detection chip 100 can be used to perform a polymerase chain reaction (for example, a digital polymerase chain reaction), and further can be used for a detection process subsequent to the reaction.

For example, as illustrated in FIG. 2 and FIG. 3, the heating electrode 12 is located on the first substrate 10, and the heating electrode 12 can receive an electrical signal (for example, a voltage signal). Therefore, when a current flows through the heating electrode 12, heat is generated and conducted into at least some of the micro-reaction chambers 110 for usage in the polymerase chain reaction. For example, the heating electrode 12 may be made of a conductive material with a large resistivity, so that the heating electrode 12 can generate a larger amount of heat in the case where a smaller electrical signal is provided, so as to improve the energy conversion rate. For example, the heating electrode 12 may be made of a transparent conductive material, such as indium tin oxide (ITO), tin oxide, or the like, or may be made of other suitable materials, such as metal or the like, which is not limited in the embodiments of the present disclosure. For example, the heating electrode 12 is a planar electrode, and for example, a conductive material is used to uniformly form on the first substrate 10, so as to allow the plurality of micro-reaction chambers 110 to be uniformly heated. Certainly, the embodiments of the present disclosure are not limited to this case, and the heating electrode 12 may also have a specific shape or pattern, such as a broken line shape, an arc shape, etc., which may be determined according to the distribution manner of the plurality of micro-reaction chambers 110.

The micro-cavity defining layer 11 is located on the first substrate 10 and is located on the heating electrode 12, that is, the heating electrode 12 is closer to the first substrate 10 than the micro-cavity defining layer 11. The micro-cavity defining layer 11 defines the plurality of micro-reaction chambers 110, and adjacent micro-reaction chambers 110 are at least partially spaced from each other (for example, by a partition wall). For example, each of the plurality of micro-reaction chambers 110 includes a reaction trap, and the reaction trap includes a sidewall 1101 and a bottom 1102. The reaction trap provides an accommodating space for the reaction system liquid, and the droplet of the reaction system liquid that enters the micro-cavity defining layer 11 and moves into the reaction trap can remain in the reaction trap in a relatively stable state. For example, the reaction trap may be a micro-reaction groove, a micro-reaction hollow, or the like, as long as the reaction trap has a space capable of containing the reaction system liquid, and the embodiments of the present disclosure are not limited in this aspect.

For example, shapes of the plurality of micro-reaction chambers 110 may be the same, and the three-dimensional shape of each micro-reaction chamber 110 is, for example, an approximate cylinder, that is, as illustrated in a partially enlarged view A in FIG. 3 and FIG. 2, a cross section in a direction perpendicular to the first substrate 10 is approximately rectangular and a cross section in a plane parallel to the first substrate 10 is approximately circular. For example, the diameter of the bottom surface of the cylinder ranges from 1 μm to 100 μm, for example, 20 μm to 50 μm. The height of the cylinder ranges from 5 μm to 100 μm, for example, 30 μm to 50 μm. For example, in some examples, the diameter of the bottom surface of the cylinder is 8 μm, and the height of the cylinder is 9.8 μm. It should be noted that shapes of at least some of the micro-reaction chambers 110 may also be different.

The shape of the micro-reaction chamber 110 may be designed according to practical requirements. For example, the shape of each micro-reaction chamber 110 may also be a frustum of a cone, a cuboid, a polygonal prism, a sphere, an ellipsoid, etc., which is not limited in the embodiments of the present disclosure. For example, the shape of the cross section of the micro-reaction chamber 110 in the plane parallel to the first substrate 10 may be an ellipse, a triangle, a polygon, an irregular shape, or the like, and the cross section in the direction perpendicular to the first substrate 10 may be in a shape of a polygon, such as a square, a circle, a parallelogram, a trapezoid, or the like.

For example, as illustrated in FIG. 2, the plurality of micro-reaction chambers 110 are uniformly distributed on the first substrate 10. For example, on the first substrate 10, the plurality of micro-reaction chambers 110 are arranged in an array along a first direction X and a second direction Y. In this way, the fluorescent image obtained when the optical detection is performed on the detection chip 100 in the subsequent phase can be regular and orderly, so as to obtain the detection result quickly and accurately. Certainly, the embodiments of the present disclosure are not limited to this case, and the plurality of micro-reaction chambers 110 may also be unevenly distributed on the first substrate 10 or may be arranged in other manners, which are not limited in the embodiments of the present disclosure. For example, the number of the plurality of micro-reaction chambers 110 may be 2,000 to 1,000,000. For example, in some examples, the number of the plurality of micro-reaction chambers 110 is 40,000 to 100,000. Therefore, the detection throughput of the detection chip 100 is high.

It should be noted that, in the embodiments of the present disclosure, the size and number of the micro-reaction chambers 110 may be determined according to practical requirements, and the size and number of the micro-reaction chambers 110 may be related to the size of the detection chip 100 and the size of the first substrate 10. In the case where the size of the micro-reaction chamber 110 is constant, the larger the number of the micro-reaction chambers 110 is, the larger the size of the detection chip 100 and the size of the first substrate 10 are.

Because target molecules (i.e., DNA templates) in the reaction system liquid are sufficiently diluted, after the reaction system liquid enters each micro-reaction chamber 110, the number of target molecules (i.e., DNA templates) in each micro-reaction chamber 110 is less than or equal to 1, that is, each micro-reaction chamber 110 includes only one target molecule or does not include the target molecule, so as to obtain an accurate detection result in the subsequent phase.

For example, the material of the micro-cavity defining layer 11 is a photoresist that can be processed in a thick film. The photoresist can be formed on the first substrate 10 by spin coating, and has a large thickness. For example, the thickness of the micro-cavity defining layer 11 may range from 5 μm to 100 μm, for example, 9.8 μm. For example, the micro-cavity defining layer 11 may be patterned and etched to obtain the plurality of micro-reaction chambers 110, and the plurality of micro-reaction chambers 110 are isolated from each other.

For example, the orthographic projections of the plurality of micro-reaction chambers 110 on the first substrate 10 are within the orthographic projection of the heating electrode 12 on the first substrate 10. Here, the orthographic projection refers to a projection on the first substrate 10 in the direction perpendicular to the first substrate 10. For example, as illustrated in FIG. 2, in the direction perpendicular to the first substrate 10, the projections of the plurality of micro-reaction chambers 110 on the first substrate 10 are within the projection of the heating electrode 12 on the first substrate 10, and the projection of the heating electrode 12 is larger than the projections of the plurality of micro-reaction chambers 110. In this way, each micro-reaction chamber 110 can be heated by the heating electrode 12. Because of the heat radiation effect of the edge of the heating electrode 12, the working temperature of the edge region of the heating electrode 12 is lower than the working temperature of the central region of the heating electrode 12. Therefore, the above arrangement allows the micro-reaction chambers 110 to be heated by the portion, where the working temperature is uniform, of the heating electrode 12, and avoids the micro-reaction chambers 110 from being heated by the edge region (for example, regions from the edge at a distance of 5 mm, 8 mm, or other suitable size) of the heating electrode 12, so that the plurality of micro-reaction chambers 110 are heated more uniformly and the temperature consistency is better, thereby facilitating the effective amplification reaction of the reaction system liquid in the micro-reaction chambers 110.

In the embodiments of the present disclosure, by providing the heating electrode 12 in the detection chip 100 (for example, integrating the heating electrode 12 on the first substrate 10), the micro-reaction chambers 110 of the detection chip 100 can be effectively heated, thereby implementing the temperature control of the micro-reaction chambers 110 without external heating equipment and implementing a high integration. In addition, compared with some detection chips which need to drive the droplet to move and sequentially pass through a plurality of temperature regions, the detection chip 100 can implement temperature cycling without the driving operation on the droplet, which is simple to operate and has low production costs.

For example, as illustrated in FIG. 3, the detection chip 100 further includes a hydrophilic layer 14, and the hydrophilic layer 14 has the characteristics of hydrophilicity and lipophobicity. For example, the hydrophilic layer 14 covers the sidewall 1101 and the bottom 1102 of each of the plurality of micro-reaction chambers 110. Because the surface of the micro-reaction chamber 110 (that is, the sidewall 1101 and the bottom 1102 of the micro-reaction chamber 110) is provided with the hydrophilic layer 14, the hydrophilicity of the micro-reaction chamber 110 is improved, and in the case where no external driving force is applied to the reaction system liquid, the reaction system liquid can automatically enter each of the micro-reaction chambers 110 gradually based on the capillary phenomenon, thereby implementing auto-injection.

Figure 6A:
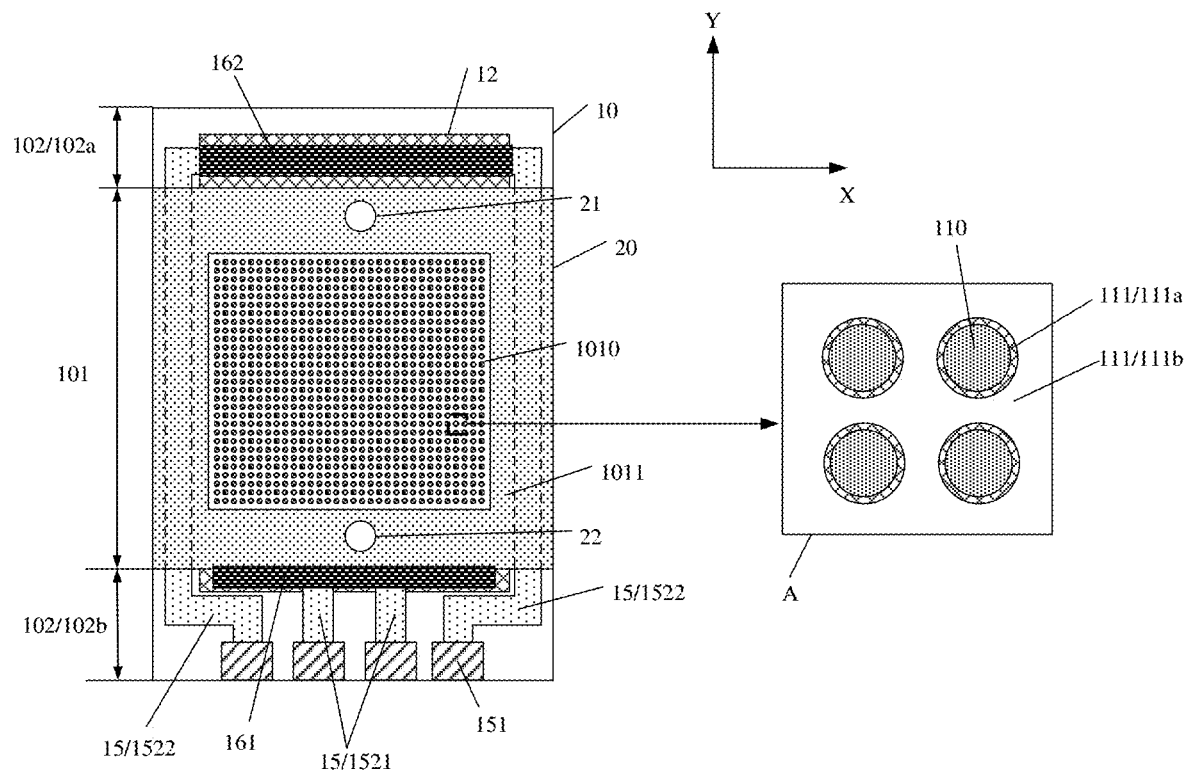
FIG. 6A is a schematic planar diagram of another detection chip provided by some embodiments of the present disclosure.
Figure 6B:
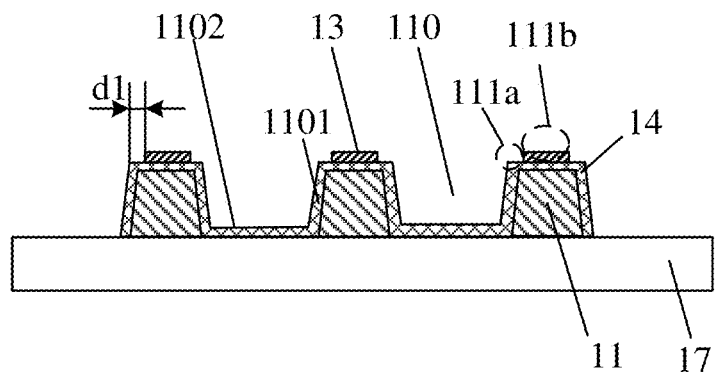
FIG. 6B is a schematic partial cross-sectional structural diagram of another detection chip provided by some embodiments of the present disclosure.
Figure 6C:
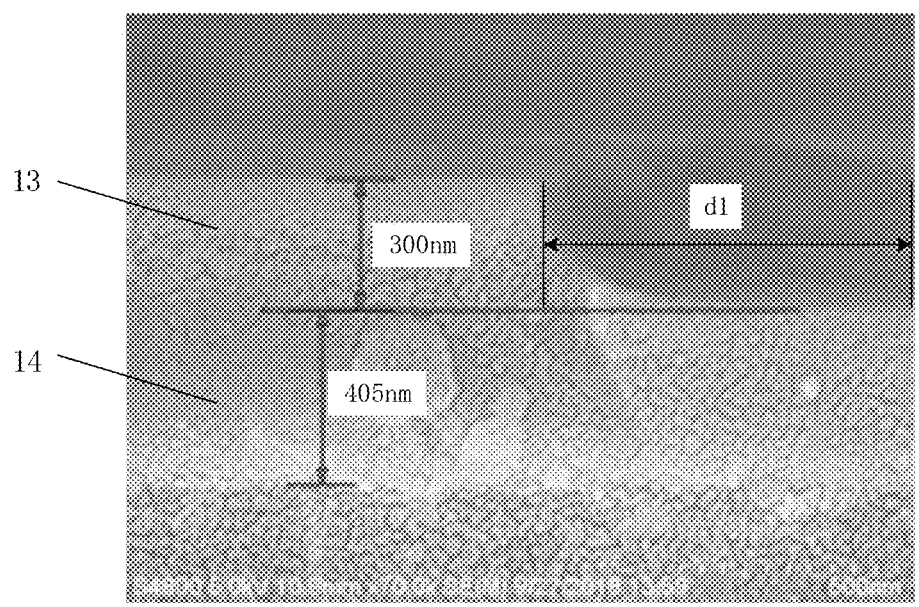
FIG. 6C is a schematic scanning electron microscope diagram of a micro-cavity defining layer, a hydrophilic layer, and a hydrophobic layer of another detection chip provided by some embodiments of the present disclosure.

For example, in some embodiments, as illustrated in FIG. 3, the hydrophilic layer 14 may further cover a surface, away from the first substrate 10, of the micro-cavity defining layer 11, that is, the hydrophilic layer 14 is also provided on the spacing portion between the plurality of micro-reaction chambers 110. In this way, the hydrophilic layer 14 can completely cover the micro-cavity defining layer 11, so that the reaction system liquid can more easily enter each of the micro-reaction chambers 110, and the injection speed can be improved. It should be noted that the hydrophilic layer 14 may be provided in various manners. For example, the hydrophilic layer 14 may also be provided in the manner below which is illustrated in FIG. 6A to FIG. 6C, and details may be with reference to the following content and are not described herein again.

For example, the material of the hydrophilic layer 14 is silicon oxide, such as silicon dioxide (SiO2). Certainly, the embodiments of the present disclosure are not limited to this case, and the hydrophilic layer 14 may also be made of other suitable inorganic or organic materials, as long as the surface, away from the micro-cavity defining layer 11, of the hydrophilic layer 14 is hydrophilic. For example, the hydrophilic layer 14 can be directly prepared by using a hydrophilic material. For another example, the hydrophilic layer 14 may be made of a material having no hydrophilicity, and in this case, the surface, away from the micro-cavity defining layer 11, of the hydrophilic layer 14 needs to be performed with a hydrophilic treatment, so as to enable the surface, away from the micro-cavity defining layer 11, of the hydrophilic layer 14 to be hydrophilic. For example, in the case where a non-hydrophilic material is used, such as silicon nitride, the surface can be performed with the hydrophilic treatment, for example, the gelation modification method, the ultraviolet radiation method, the plasma method, etc., and for example, the surface of the non-hydrophilic material can be provided with hydrophilic radical groups, so as to enable the surface to be hydrophilic.

For example, as illustrated in FIG. 3, the detection chip 100 further includes a second substrate 20 and a hydrophobic layer 13. The second substrate 20 is disposed opposite to the first substrate 10 and plays a role in protection, supporting, isolation, etc. The hydrophobic layer 13 has the characteristics of hydrophobicity and lipophilicity, and is located on a side, facing the first substrate 10, of the second substrate 20. The micro-cavity defining layer 11 is located on a side, facing the second substrate 20, of the first substrate 10, and a surface, away from the first substrate 10, of the micro-cavity defining layer 11 faces the second substrate 20. By providing the hydrophobic layer 13, the reaction system liquid can more easily enters each of the micro-reaction chambers 110. It should be noted that the hydrophobic layer 13 may be provided in various manners, and for example, may also be provided in the manner below which is illustrated in FIG. 6A to FIG. 6C, and details may be with reference to the following content and are not described herein again.

For example, both the first substrate 10 and the second substrate 20 are glass substrates. The detection chip 100 can be manufactured by using a micro-processing method of combining glass base with semiconductor process, thereby implementing large-scale mass production and greatly reducing corresponding production costs. It should be noted that, in various embodiments of the present disclosure, the first substrate 10 and the second substrate 20 may also adopt other suitable substrates, which are not limited in the embodiments of the present disclosure. For example, the shape of the first substrate 10 and the shape of the second substrate 20 are both rectangle. For example, in some examples, the size of the first substrate 10 is 3.2 cm*4.5 cm, and the size of the second substrate 20 is 3.2 cm*3 cm.

For example, the material of the hydrophobic layer 13 is a resin or silicon nitride, and for example, may be a commercially available epoxide resin of a model of DL-1001C. The hydrophobic layer 13 may also be made of other suitable inorganic or organic materials, as long as the side, facing the first substrate 10, of the hydrophobic layer 13 is hydrophobic. For example, the hydrophobic layer 13 may be directly prepared by using a hydrophobic material. For another example, the hydrophobic layer 13 may be made of a material without hydrophobicity, and in this case, the surface, facing the first substrate 10, of the hydrophobic layer 13 needs to be performed with a hydrophobic treatment, so as to enable the surface, facing the first substrate 10, of the hydrophobic layer 13 to be hydrophobic.

In the embodiments of the present disclosure, the hydrophilic layer 14 and the hydrophobic layer 13 cooperate to adjust the surface contact angle of the droplet of the reaction system liquid, so as to allow the detection chip 100 to implement self-absorption liquid sample injection and oil sealing. For example, in the detection chip 100, the hydrophobic performance outside the micro-reaction chamber 110 is improved by the hydrophobic layer 13, so that the external of the micro-reaction chamber 110 (for example, the surface, facing the micro-reaction chamber 110, of the second substrate 20) is hydrophobic, and the internal surface of the micro-reaction chamber 110 has good hydrophilicity, thereby allowing the reaction system liquid to infiltrate from the outside of the micro-reaction chamber 110 to the inside of the micro-reaction chamber 110. Therefore, under the function of the hydrophilic layer 14 and the hydrophobic layer 13, the reaction system liquid can more easily enter each of the micro-reaction chambers 110.

For example, as illustrated in FIG. 3, the detection chip 100 further includes a control electrode 15 and a first insulating layer 16. The control electrode 15 is located on the first substrate 10, the first insulating layer 16 covers the control electrode 15, and the heating electrode 12 is located on the first insulating layer 16. For example, the first insulating layer 16 includes a via hole 160 which penetrates the first insulating layer 16, the control electrode 15 is electrically connected to the heating electrode 12 through the via hole 160, and the control electrode 15 is configured to apply an electrical signal (e.g., a voltage signal) to the heating electrode 12. After the heating electrode 12 receives the electric signal, the heating electrode 12 can generate heat under the action of the electric signal, thereby heating the micro-reaction chambers 110. It should be noted that the first insulating layer 16 may further cover a portion, which is not blocked by the control electrode 15, of the first substrate 10.

For example, the via hole 160 exposes a portion of the control electrode 15, so that the heating electrode 12 can be electrically connected to the control electrode 15 through the via hole 160. The shape of the via hole 160 may be a cylinder, a frustum of a cone, or the like. For example, the control electrode 15 may be electrically connected to the heating electrode 12 through one or more via holes 160. In the case where the electrical connection is implemented through a plurality of via holes 160, the connection resistance can be effectively reduced, and the energy loss can be reduced. In the case where the electrical connection is implemented through one via hole 160, the manufacturing process can be simplified.

For example, the number of the control electrodes 15 may be one or more than one, which is not limited in the embodiments of the present disclosure. In the case where a plurality of control electrodes 15 are used to apply the electrical signal to the heating electrode 12, different portions of the heating electrode 12 can simultaneously receive the electrical signal, so that the heat generation of the heating electrode 12 is more uniform. For example, in the case where there are a plurality of control electrodes 15, the first insulating layer 16 may include a plurality of via holes 160, and each of the via holes 160 exposes a portion of each control electrode 15, so that the heating electrode 12 is electrically connected to the plurality of control electrodes 15 through the plurality of via holes 160, respectively. For example, the plurality of control electrodes 15 are in one-to-one correspondence with the plurality of via holes 160. For another example, the number of the plurality of via holes 160 may also be greater than the number of the plurality of control electrodes 15, and each of the control electrodes 15 is electrically connected to the heating electrode 12 through one or more via holes 160.

It should be noted that, in the example illustrated in FIG. 3, the heating electrode 12 and the control electrode 15 are located in different layers. In some other embodiments, the heating electrode 12 and the control electrode 15 may also be located in the same layer. In this case, in the detection chip 100, the first insulating layer 16 may be omitted, and the heating electrode 12 may be overlapped with the control electrode 15 to implement the electric connection.

For example, the resistance value of the heating electrode 12 is greater than the resistance value of the control electrode 15, so that under the action of the same electrical signal, the heating electrode 12 generates more heat to heat the micro-reaction chambers 110, and the control electrode 15 generates less heat, thereby reducing the energy loss. For example, the control electrode 15 may be made of a material with a lower resistivity, thereby reducing the energy loss of the control electrode 15. The control electrode 15 may be made of a metal material. The metal material may be, for example, copper or a copper alloy, aluminum or an aluminum alloy, or the like, and the control electrode 15 may be a single metal layer or composite metal layers, and the embodiments of the present disclosure are not limited in this aspect.

For example, in some embodiments of the present disclosure, the heating electrode 12 is made of indium tin oxide (ITO) or tin oxide, and the control electrode 15 is made of a metal material. Because ITO is not easy to be oxidized, ITO can prevent the portion, exposed to the air, of the heating electrode 12 from being oxidized, thereby avoiding problems such as uneven heating or increased power consumption caused by the oxidation of the heating electrode 12. The control electrode 15 is covered by the first insulating layer 16, and therefore, even through the control electrode 15 is made of a metal material, the problem of oxidation is unlikely to occur.

For example, in order to facilitate the electrical connection between the control electrode 15 and an additionally provided device to enable the control electrode 15 to receive the electrical signal (such as a voltage signal), the control electrode 15 may further include a contact portion 151 (as illustrated in FIG. 2, for example, a pad region), and the contact portion 151 is not covered by the first insulating layer 16. For example, the contact portion 151 has a large square shape, so as to facilitate the contact and connection with a probe or an electrode in the additionally provided device. The contact portion 151 has a large contact area, and can stably receive the electrical signal. In this way, the detection chip 100 can implement plug-and-play, and the operation is simple and convenient. For example, in the case where the control electrode 15 is made of a metal material, the contact portion 151 may be processed by electroplating, thermal spraying, or vacuum plating, so as to form a metal protective layer on the surface of the contact portion 151 to prevent the contact portion 151 from being oxidized while the conductive performance cannot be affected.

For example, as illustrated in FIG. 3, the detection chip 100 further includes a second insulating layer 17. The second insulating layer 17 is located between the heating electrode 12 and the micro-cavity defining layer 11, that is, the second insulating layer 17 is located on a side, away from the first substrate 10, of the heating electrode 12, and the micro-cavity defining layer 11 is located on a side, away from the heating electrode 12, of the second insulating layer 17. The second insulating layer 17 is used for protecting the heating electrode 12, providing an insulation function, preventing the liquid from eroding the heating electrode 12, slowing down the aging of the heating electrode 12, and providing a planarization function.

For example, the first insulating layer 16 and the second insulating layer 17 may be made of the same insulating material, for example, an inorganic insulating material or an organic insulating material. For example, the first insulating layer 16 and the second insulating layer 17 may be made of silicon dioxide, silicon nitride, or the like.

For example, as illustrated in FIG. 2 and FIG. 3, the first substrate 10 includes a reaction region 101 and a peripheral region 102, and the peripheral region 102 is at least partially around the reaction region 101. For example, in some embodiments, in the second direction Y, the peripheral region 102 includes a first sub-region 102a and a second sub-region 102b located on different sides of the reaction region 101, respectively. For another example, in some other embodiments, the peripheral region 102 is completely around the reaction region 101, that is, the peripheral region 102 is annular and surrounds the reaction region 101. For example, in this case, in the second direction Y, the peripheral region 102 includes a first sub-region 102a and a second sub-region 102b located on different sides of the reaction region 101, respectively, and in the first direction X, the peripheral region 102 further includes a third sub-region and a fourth sub-region on different sides of the reaction region 101, respectively. The first sub-region 102a is in communication with both the third sub-region and the fourth sub-region, and the second sub-region 102b is also in communication with both the third sub-region and the fourth sub-region, so that the peripheral region 102 is around the reaction region 101.

For example, in the example illustrated in FIG. 2, the size of the second substrate 20 is smaller than the size of the first substrate 10, and the second substrate 20 covers the reaction region 101. For example, an orthographic projection of the second substrate 20 on the first substrate 10 may completely coincide with the reaction region 101. It should be noted that the embodiments of the present disclosure are not limited to this case. In some other examples, the size of the second substrate 20 may be the same as the size of the first substrate 10. In this case, the second substrate 20 covers the reaction region 101 and the peripheral region 102, and for example, an orthographic projection of the second substrate 20 on the first substrate 10 may completely coincide with the first substrate 10.

For example, the control electrode 15 and the via hole 160 are located in the peripheral region 102, and the heating electrode 12 is located in the reaction region 101 and the peripheral region 102. For example, the reaction region 101 further includes a functional region 1010, and the micro-cavity defining layer 11 is located in the functional region 1010. For example, an orthographic projection of the heating electrode 12 on the first substrate 10 completely covers the functional region 1010 of the reaction region 101, that is, the functional region 1010 is within the orthographic projection of the heating electrode 12 on the first substrate 10, thereby ensuring that the heating electrode 12 can heat each of the micro-reaction chambers 110.

For example, in the case where the voltage signal (e.g., a high voltage signal) is applied to the heating electrode 12 through only one control electrode 15, and a ground voltage is applied to the heating electrode 12 through another control electrode 15, for example, a current path in the second direction Y is formed on the heating electrode 12 and enables the heating electrode 12 to generate heat. Because the heating electrode 12 itself has a large resistance value, a large voltage drop may be generated in a direction extending along the first direction X from the connection portion between the heating electrode 12 and the control electrode 15, so that the heating electrode 12 can be divided into a first partial electrode and a second partial electrode arranged in the first direction X. The first partial electrode receives a larger voltage signal, and for example, the first partial electrode is the electrode portion at the connection portion between the heating electrode 12 and the control electrode 15. The second partial electrode receives a smaller voltage signal, and for example, the second partial electrode is the electrode portion away from the above connection portion in the first direction X. Accordingly, the current in the heating electrode 12 is not uniform, the current in the first partial electrode is larger and generates more heat, and the current in the second partial electrode is smaller and generates less heat. Therefore, when the heating electrode 12 is used for heating, temperatures at different positions of the functional region 1010 may be different, so that the temperatures of the micro-reaction chambers 110 at different positions are different, which ultimately affects the amplification reaction of the reaction system liquid in the micro-reaction chambers 110 and affects the accuracy of the detection effect.

In view of the above problems, as illustrated in FIG. 2, a plurality of control electrodes 15 may be provided in the detection chip 100, and the plurality of control electrodes 15 may simultaneously transmit the same electrical signal to the heating electrode 12. For example, the plurality of control electrodes 15 may be uniformly distributed in the peripheral region 102, and the plurality of control electrodes 15 may simultaneously apply the electrical signal to the heating electrodes 12 at different positions, thereby improving temperature uniformity at different positions in the functional region 1010 and allowing the heat generated in different portions of the heating electrode 12 to be approximately the same, so that the temperatures at different positions in the functional region 1010 are approximately the same. As illustrated in FIG. 2, in some examples, the detection chip 100 may include ten control electrodes 15, five of the control electrodes 15 are located in the first sub-region 102a of the peripheral region 102 and are uniformly arranged along the first direction X, and the other five control electrodes 15 are located in the second sub-region 102b of the peripheral region 102 and are uniformly arranged along the first direction X. The five control electrodes 15 in the first sub-region 102a or in the second sub-region 102b apply the voltage signal (e.g., a high voltage signal) to the heating electrode 12, and the other five control electrodes 15 in the second sub-region 102b or in the first sub-region 102a apply, e.g., the ground voltage to the heating electrode 12, so as to form a current path on the heating electrode 12, which can improve the uniformity of the current in the heating electrode 12 and further improve the temperature uniformity.

It should be noted that in the case where the peripheral region 102 further includes the third sub-region and the fourth sub-region located on different sides of the reaction region 101, respectively, in the first direction X, the third sub-region and the fourth sub-region may also be provided with a plurality of control electrodes 15. The embodiments of the present disclosure do not limit, e.g., the number and arrangement positions of the control electrodes 15.

For example, as illustrated in FIG. 3, the detection chip 100 further includes a plurality of spacers 18. The plurality of spacers 18 are disposed in the peripheral region 102 and are located between the first substrate 10 and the second substrate 20. The plurality of spacers 18 are configured to maintain a distance between the first substrate 10 and the second substrate 20, so as to provide a space for the flowing of the reaction system liquid. For example, in some embodiments, some of the spacers 18 may also be disposed in the reaction region 101, for example, distributed at a plurality of positions in the reaction region 101, thereby improving the compressive strength of the detection chip 100 and preventing the detection chip 100 from being damaged by the external force applied to the reaction region 101. For example, the sizes and shapes of the plurality of spacers 18 may be the same, thereby improving the thickness uniformity of the detection chip 100. For another example, the sizes and shapes of the plurality of spacers 18 can also be determined according to the probable force applied to the detection chip 100. For example, the sizes of the spacers 18 at the periphery and center of the detection chip 100 are relatively large, and the sizes of the spacers 18 at other positions are relatively small.

For example, in the direction perpendicular to the first substrate 10, the height of the spacer 18 is greater than the height of the micro-cavity defining layer 11. The first substrate 10, the micro-cavity defining layer 11, and a frame sealant including the spacers 18 together define a sample injection channel and a sample output channel of the droplet of the reaction system liquid, thereby ensuring that the droplet can move to each of the micro-reaction chambers 110 and the droplet that does not enter the micro-reaction chambers 110 can flow out of the space between the first substrate 10 and the second substrate 20. For example, in some embodiments, the height of the spacer 18 is greater than the height of the micro-cavity defining layer 11 by 30% or 50%, and the specific proportional relationship between the two heights can be determined according to practical requirements, which is not limited in the embodiments of the present disclosure.

For example, the material of the spacer 18 may be a curable organic material, such as a heat-curable material or a light-curable material, or may also be an ultraviolet (UV) curable acrylic resin or other suitable materials. The shape of the spacer 18 may be a sphere. In this case, the spacers 18 may be uniformly mixed in the frame sealant, and then the first substrate 10 and the second substrate 20 are sealed and cured by the frame sealant, so that the first substrate 10 and the second substrate 20 form a cell. In this way, the spacers 18 mixed in the frame sealant can control the distance between the first substrate 10 and the second substrate 20. The embodiments of the present disclosure include this case but are not limited to this case, and the shape of the spacer 18 may also be any suitable shape such as a column shape, an ellipsoid shape, etc.

For example, in some embodiments, as illustrated in FIG. 3, the detection chip 100 further includes a first temperature sensor 30. The first temperature sensor 30 is disposed on a side, away from the second substrate 20, of the first substrate 10 (that is, a side, away from the micro-cavity defining layer 11, of the first substrate 10), and is located in the reaction region 101. The first temperature sensor 30 is configured to detect the temperature of the reaction region 101. For example, the temperature of the reaction region 101 needs to be maintained at a predetermined temperature (for example, 95° C., 55° C., 72° C., or the like). In this case, the first temperature sensor 30 can detect the temperature of the reaction region 101 in real time, and then the temperature of the reaction region 101 can be adjusted through the heating electrode 12 in real time, so as to keep the temperature of the reaction region 101 at the predetermined temperature, thereby preventing the temperature of the reaction region 101 from being too high or too low to affect the amplification reaction. For example, the first temperature sensor 30 may be various types of temperature sensors, such as a contact-type temperature sensor or a non-contact-type temperature sensor, a thermocouple temperature sensor or an infrared temperature sensor, and the like.

For example, as illustrated in FIG. 2 and FIG. 3, the detection chip 100 further includes at least one sample inlet 21 and at least one sample outlet 22, and both the sample inlet 21 and the sample outlet 22 penetrate the second substrate 20 and the hydrophobic layer 13. For example, the reaction system liquid can be injected into the sample inlet 21 through a micro-injection pump or a pipette, and then enter each of the micro-reaction chambers 110 in liquid self-absorption manner.

For example, the reaction region 101 further includes a non-functional region 1011, and the sample inlet 21 and the sample outlet 22 are both located in the non-functional region 1011 and on different sides of the functional region 1010, for example, symmetrically distributed on different sides of the functional region 1010. For example, as illustrated in FIG. 2, in the second direction Y, the sample inlet 21 and the sample outlet 22 are located on different sides of the functional region 1010, respectively. For example, the sample inlet 21 and the sample outlet 22 are distributed symmetrically with respect to the first direction X, so that the reaction system liquid can flow more uniformly in the detection chip 100, thereby facilitating the reaction system liquid entering each of the micro-reaction chambers 110. Certainly, the embodiments of the present disclosure are not limited to this case, and the sample inlet 21 and the sample outlet 22 may also be symmetrically distributed with respect to the second direction Y or any other directions. It should be noted that the sample inlet 21 and the sample outlet 22 may both be located in the functional region 1010.

Figure 4A:
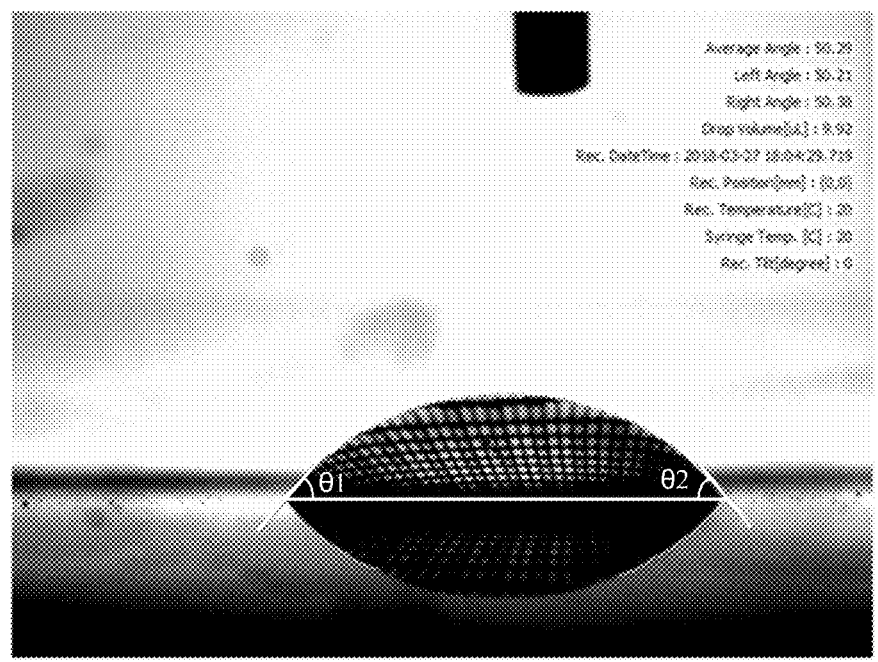
FIG. 4A is a schematic diagram of a surface hydrophilicity and hydrophobicity test performed on a micro-reaction chamber before surface modification provided by some embodiments of the present disclosure.
Figure 4B:
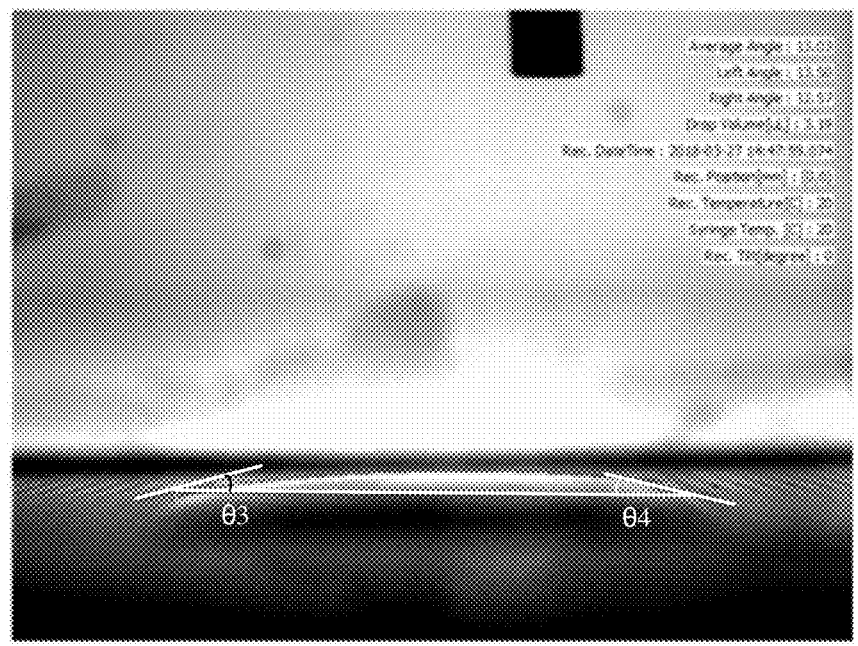
FIG. 4B is a schematic diagram of a surface hydrophilicity and hydrophobicity test performed on a micro-reaction chamber after surface modification provided by some embodiments of the present disclosure.

FIG. 4A is a schematic diagram of a surface hydrophilicity and hydrophobicity test performed on a micro-reaction chamber before surface modification provided by some embodiments of the present disclosure, and FIG. 4B is a schematic diagram of a surface hydrophilicity and hydrophobicity test performed on a micro-reaction chamber after surface modification provided by some embodiments of the present disclosure. Here, the term "micro-reaction chamber before surface modification" refers to a micro-reaction chamber without a hydrophilic layer provided at the bottom and on the sidewall of the micro-reaction chamber, and is referred to as a first micro-reaction chamber below; and the term "micro-reaction chamber after surface modification" refers to a micro-reaction chamber with a hydrophilic layer provided at the bottom and on the sidewall of the micro-reaction chamber, that is, the micro-reaction chamber 110 in the detection chip 100 provided by the embodiments of the present disclosure, and is referred to as a second micro-reaction chamber below.

For example, in the testing process illustrated in FIG. 4A and FIG. 4B, deionized water is used as a test droplet, and the contact angle of the droplet on the surface (bottom or sidewall) of the micro-reaction chamber is tested. As illustrated in FIG. 4A, the volume of the first test droplet is 9.92 μL. For the first micro-reaction chamber, the left contact angle θ1 between the first test droplet and the surface of the first micro-reaction chamber is about 50.38°, and the right contact angle θ2 between the first test droplet and the surface of the first micro-reaction chamber is about 50.21°, so that the average contact angle between the first test droplet and the surface of the first micro-reaction chamber is about 50.29°. As illustrated in FIG. 4B, the volume of the second test droplet is 3.19 μL. For the second micro-reaction chamber, the left contact angle θ3 between the second test droplet and the surface of the second micro-reaction chamber is about 12.57°, and the right contact angle θ4 between the second test droplet and the surface of the second micro-reaction chamber is about 13.50°, so that the average contact angle between the second test droplet and the surface of the second micro-reaction chamber is about 13.03°. It can be seen that, in some embodiments of the present disclosure, because the surface of the micro-reaction chamber 110 is provided with the hydrophilic layer 14, the hydrophilicity is greatly improved, and the contact angle between the droplet and the surface of the micro-reaction chamber 110 is relatively small.

Figure 5A:
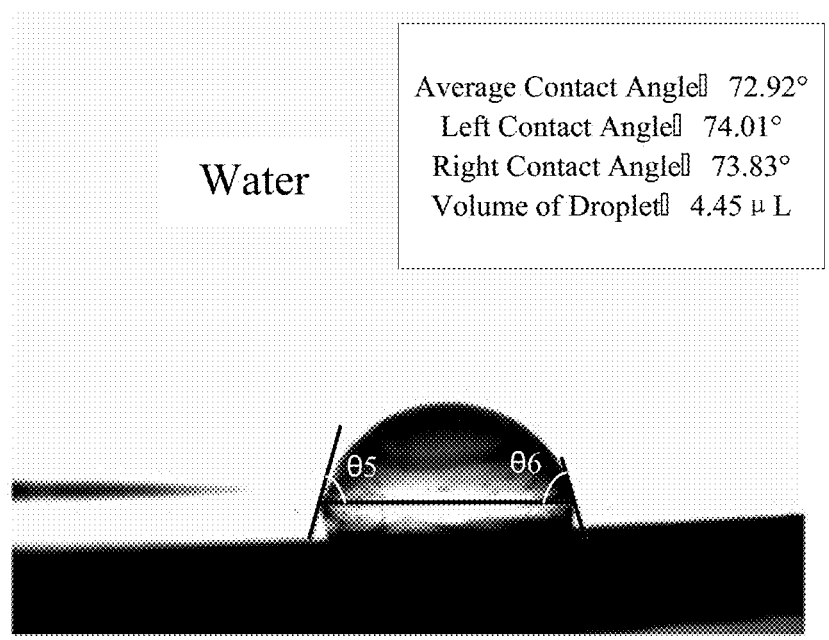
FIG. 5A is a schematic diagram of performing a surface hydrophilicity and hydrophobicity test on a second substrate of a detection chip provided by some embodiments of the present disclosure.
Figure 5B:
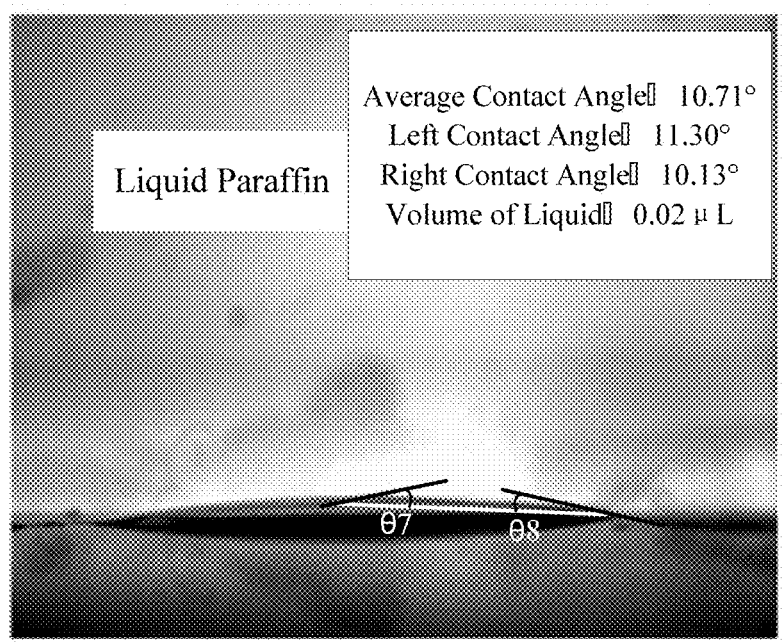
FIG. 5B is a schematic diagram of performing a surface hydrophilicity and hydrophobicity test on a second substrate of a detection chip provided by some other embodiments of the present disclosure.

FIG. 5A is a schematic diagram of performing a surface hydrophilicity and hydrophobicity test on a second substrate of a detection chip provided by some embodiments of the present disclosure, and FIG. 5B is a schematic diagram of performing a surface hydrophilicity and hydrophobicity test on a second substrate of a detection chip provided by some other embodiments of the present disclosure.

For example, in the testing process illustrated in FIG. 5A, the droplet of deionized water is used, and the contact angle of the droplet on the surface of the hydrophobic layer 13 on the second substrate 20 is tested. For example, the volume of the droplet is 4.45 µL, the left contact angle θ5 between the droplet and the surface of the hydrophobic layer 13 on the second substrate 20 is about 73.83°, and the right contact angle θ6 between the droplet and the surface of the hydrophobic layer 13 on the second substrate 20 is about 74.01°, so that the average contact angle between the droplet and the surface of the hydrophobic layer 13 on the second substrate 20 is about 72.92°. In the testing process illustrated in FIG. 5B, liquid paraffin is used, and the contact angle of the liquid paraffin on the surface of the hydrophobic layer 13 on the second substrate 20 is tested. For example, the volume of the liquid paraffin is 0.02 µL, the left contact angle θ7 between the liquid paraffin and the surface of the hydrophobic layer 13 on the second substrate 20 is about 10.13°, and the right contact angle θ8 between the liquid paraffin and the surface of the hydrophobic layer 13 on the second substrate 20 is about 11.30°, so that the average contact angle between the liquid paraffin and the surface of the hydrophobic layer 13 on the second substrate 20 is about 10.71°. It can be seen that, in some embodiments of the present disclosure, because the surface of the second substrate 20 is provided with the hydrophobic layer 13, the hydrophobicity is greatly improved, and the contact angle between the droplet and the surface of the hydrophobic layer 13 on the second substrate 20 is relatively large while the contact angle between the liquid paraffin and the surface of the hydrophobic layer 13 on the second substrate 20 is relatively small.

FIG. 6A is a schematic planar diagram of another detection chip provided by some embodiments of the present disclosure, and FIG. 6B is a schematic partial cross-sectional structural diagram of another detection chip provided by some embodiments of the present disclosure. For example, as illustrated in FIG. 6A and FIG. 6B, except the difference in the arrangement of the hydrophilic layer 14 and the hydrophobic layer 13, and the difference in the arrangement of the control electrode 15, the detection chip 100 of this embodiment is basically the same as the detection chip 100 illustrated in FIG. 2 and FIG. 3. In the following, the arrangement of the hydrophilic layer 14 and the hydrophobic layer 13, and the arrangement of the control electrode 15 in the detection chip 100 provided by this embodiment are described, other structures can be with reference to the related descriptions of FIG. 2 and FIG. 3, and details are not described herein again.

For example, as illustrated in FIG. 6A and FIG. 6B, each of the plurality of micro-reaction chambers 110 includes a reaction trap, and the reaction trap includes a sidewall 1101 and a bottom 1102. The micro-cavity defining layer 11 includes a spacing region 111 between the plurality of micro-reaction chambers 110. The spacing region 111 includes a first region 111a adjacent to sidewalls 1101 of the plurality of micro-reaction chambers 110, and a second region 111b non-adjacent to the sidewalls 1101 of the plurality of micro-reaction chambers 110. The hydrophilic layer 14 covers the sidewall 1101 and the bottom 1102 of each of the plurality of micro-reaction chambers 110, and further covers the first region 111a in the spacing region 111 of the micro-cavity defining layer 11. The hydrophobic layer 13 covers the second region 111b in the spacing region 111 of the micro-cavity defining layer 11.

In this way, the portion, adjacent to the micro-reaction chambers 110, of the spacing region 111 of the micro-cavity defining layer 11 can possess hydrophilicity, that is, the upper edge of the sidewall 1101 can possess hydrophilicity, so that the self-absorption effect of the reaction system liquid can be better implemented, so as to further facilitate the droplet of the reaction system liquid entering each of the micro-reaction chambers 110 (i.e., the reaction trap) and avoid liquid interference.

For example, the first region 111a is in a circular ring shape, and a width dl of the circular ring shape is 2 µm to 5 µm, for example, 3 µm. Certainly, the embodiments of the present disclosure are not limited to this case, and the first region 111a may also have other shapes, for example, the shape can be determined according to the cross-sectional shape of the micro-reaction chamber 110. For example, in the case where the cross-sectional shape of the micro-reaction chamber 110 is a rectangle, the first region 111a may be in a rectangular ring shape, and in the case where the cross-sectional shape of the micro-reaction chamber 110 is a ellipse, the first region 111a may be in an oval ring shape. The width dl of the first region 111a is also not limited and can be determined according to the required self-absorption effect and manufacturing process.

For example, the hydrophilic layer 14 may be first formed on the micro-cavity defining layer 11, and the hydrophilic layer 14 covers the sidewall 1101 and the bottom 1102 of the micro-reaction chamber 110 and further covers the spacing region 111 of the micro-cavity defining layer 11. Then, the hydrophobic layer 13 is formed on the second region 111b, thereby implementing the structure illustrated in FIG. 6A and FIG. 6B. For example, in the second region 111b, the micro-cavity defining layer 11 is covered by the hydrophilic layer 14 and the hydrophobic layer 13 which are stacked, and the hydrophobic layer 13 may be in contact with the reaction system liquid. In this way, the manufacturing process can be simplified (for example, the deposition process of the hydrophilic layer 14 is simplified without patterning the hydrophilic layer 14) and the production cost can be reduced while implementing the above structure. Certainly, the embodiments of the present disclosure are not limited to this case. In other embodiments, in the second region 111b, only one layer of the hydrophobic layer 13 may cover the second region 111b, and the stacked structure of the hydrophilic layer 14 and the hydrophobic layer 13 may not be formed, which can be determined according to the practical manufacturing process and manufacturing method.

FIG. 6C is a schematic scanning electron microscope diagram of a micro-cavity defining layer, a hydrophilic layer, and a hydrophobic layer of another detection chip provided by some embodiments of the present disclosure. For example, as illustrated in FIG. 6C, the thickness of the hydrophilic layer 14 is 405 nm, the thickness of the hydrophobic layer 13 is 300 nm, and the width dl of the first region 111a is greater than 300 nm.

For example, as illustrated in FIG. 6A, the via holes 160 in the first insulating layer 16 include a first via hole group 161 and a second via hole group 162, and each of the via hole groups includes one or more via holes penetrating the first insulating layer 16. The first via hole group 161 and the second via hole group 162 are located on two opposite sides of the peripheral region 102, respectively. For example, the first via hole group 161 is located in the second sub-region 102b, and the second via hole group 162 is located in the first sub-region 102a. The control electrode 15 includes a first control electrode group 1521 and a second control electrode group 1522. The first control electrode group 1521 is located on the same side as the first via hole group 161 in the peripheral region 102, that is, located in the second sub-region 102b. The first control electrode group 1521 is electrically connected to the heating electrode 12 through the first via hole group 161. The second control electrode group 1522 extends along the peripheral region 102 and is partially around the heating electrode 12. For example, the second control electrode group 1522 extends from the second sub-region 102b to the first sub-region 102a along the edge of the heating electrode 12, and is electrically connected to the heating electrode 12 through the second via hole group 162. For example, the control electrode 15 includes a contact portion 151, and the contact portion 151 is of a large square shape, so as to facilitate the contact connection with a probe or an electrode in an additionally provided device. The contact area is large, and the electrical signal can be stably received.

In this way, the control electrode 15 can be at least partially around the heating electrode 12, the heat loss of the heating electrode 12 can be reduced, the temperature of the reaction region 101 can be more uniform, and the heating efficiency of the heating electrode 12 can be improved, thereby reducing the power consumption.

At least one embodiment of the present disclosure further provides a reaction system, and the reaction system includes a control device and the detection chip according to any one of the embodiments of the present disclosure. The reaction system facilitates the droplet automatically entering each of the micro-reaction chambers of the detection chip, which can implement effective sample injection and avoid liquid interference, and further can effectively control the temperature of the micro-reaction chambers of the detection chip and implement the temperature cycle without performing the driving operation on the droplet or without external heating equipment, so that the reaction system has high integration, the operation is simple, and the production cost is low.

Figure 7:
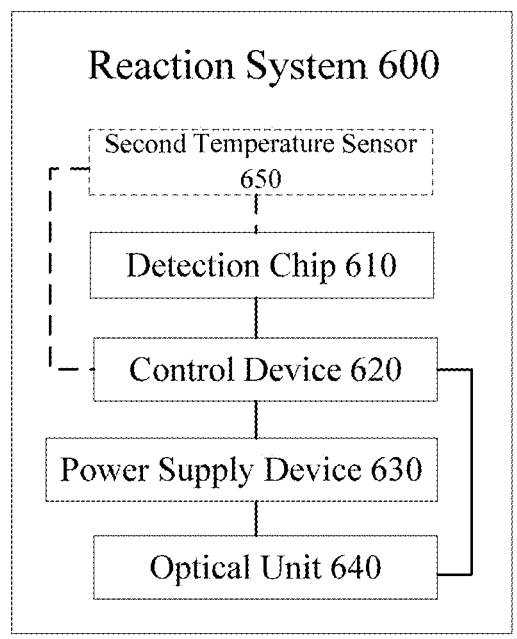
FIG. 7 is a schematic block diagram of a reaction system provided by some embodiments of the present disclosure.

FIG. 7 is a schematic block diagram of a reaction system provided by some embodiments of the present disclosure. For example, as illustrated in FIG. 7, a reaction system 600 includes a detection chip 610 and a control device 620, and further includes a power supply device 630, and the power supply device 630 supplies a signal voltage, a driving voltage, or the like to the detection chip 610 and the control device 620. The detection chip 610 is the detection chip according to any one of the embodiments of the present disclosure, and for example, is the detection chip 100 described above. The control device 620 is electrically connected to the detection chip 610, and is configured to apply an electrical signal to the detection chip 610 to drive a heating electrode of the detection chip 610. For example, the plurality of micro-reaction chambers of the detection chip 610 can contain the reaction system liquid. The control device 620 applies the electrical signal to the heating electrode of the detection chip 610 to allow the heating electrode to release heat, so as to control the temperature of the functional region of the detection chip 610 and allow the reaction system liquid to perform an amplification reaction.

For example, the control device 620 may be implemented as general or dedicated hardware, software, or firmware, and may further include, for example, a central processing unit (CPU), an embedded processor, a programmable logic controller (PLC), or the like, and the embodiments of the present disclosure are not limited in this aspect.

For example, the reaction system 600 may further include a second temperature sensor 650. For example, in the case where the detection chip 610 is substantially the same as the detection chip 100 illustrated in FIG. 3 but does not include the first temperature sensor 30, the second temperature sensor 650 needs to be provided in the reaction system 600, and the second temperature sensor 650 needs to be provided at the same position as the first temperature sensor 30 in the detection chip 100, thereby implementing the function of temperature detection. For example, the second temperature sensor 650 is disposed on a side, away from the micro-cavity defining layer, of the first substrate of the detection chip 610, and is located in the reaction region of the first substrate. The second temperature sensor 650 is configured to detect the temperature of the reaction region of the detection chip 610. For example, the second temperature sensor 650 may be various types of temperature sensors, such as a contact-type temperature sensor or a non-contact-type temperature sensor, a thermocouple temperature sensor or an infrared temperature sensor, and the like. It should be noted that, in some other embodiments, in the case where the detection chip 610 is the detection chip 100 illustrated in FIG. 3, the detection chip 100 includes the first temperature sensor 30, and therefore, there is no need to provide the second temperature sensor 650 in the reaction system 600.

For example, the reaction system 600 may further include an optical unit 640, and the optical unit 640 is configured to perform an optical detection on the detection chip 610. For example, the optical unit 640 includes a fluorescence detection device, and the fluorescence detection device is configured to perform fluorescence detection on the liquid to be detected in the plurality of micro-reaction chambers. For example, the fluorescence detection device may include a fluorescence light source and an image sensor (such as a charge-coupled device (CCD) image sensor). It should be noted that the term "liquid to be detected" is the liquid after the polymerase chain reaction is performed on the reaction system liquid, that is, the reaction system liquid which completes the amplification reaction. For example, the optical unit 640 may further include an image processing device, and the image processing device is configured to process the detection image output by the fluorescence detection device. For example, the image processing device may include a central processing unit (CPU), a graphics processing unit (GPU), or the like. For example, the control device 620 is further configured to control the fluorescence detection device and the image processing device to perform corresponding functions.

The working principle and process of the reaction system 600 are described as follows.

First, the reaction system liquid is prepared. For example, the reaction system liquid may include a cell lysis liquid, a DNA fragment sample liquid after lysis by using a DNA lyase, and a PCR amplification reagent. For example, in an example, the DNA to be detected is the No. 19 expressed region of the epidermal growth factor receptor (EGFR) gene, and accordingly, the PCR amplification reagent includes the specific PCR amplification primer of the No. 19 expressed region of the EGFR gene. For example, the volume of the reaction system liquid is 20 μL, and the reaction system liquid includes 10 μL of MIX reagents (the MIX reagents include Taq enzymes, dNPTs, and MgCl$_2$), 0.6 μL (10 mmol (mM)) of forward primers, 0.6 μL (10 mM) of reverse primers, 7.8 μL of water, and 1 μL of sufficiently diluted template DNA, so as to ensure that the amount of template DNA in each of the micro-reaction chambers is less than or equal to one.

Then, a polytetrafluoroethylene connector and a silica gel tube are installed in the sample inlet of the detection chip 610, the prepared reaction system liquid is injected into the sample inlet through a micro-injection pump or a pipette, the reaction system liquid enters the sample inlet through the polytetrafluoroethylene connector and the silica gel tube, and then the reaction system liquid enters each of the micro-reaction chambers through liquid self-absorption under the cooperation of the hydrophilic layer and the hydrophobic layer.

Figure 8A:
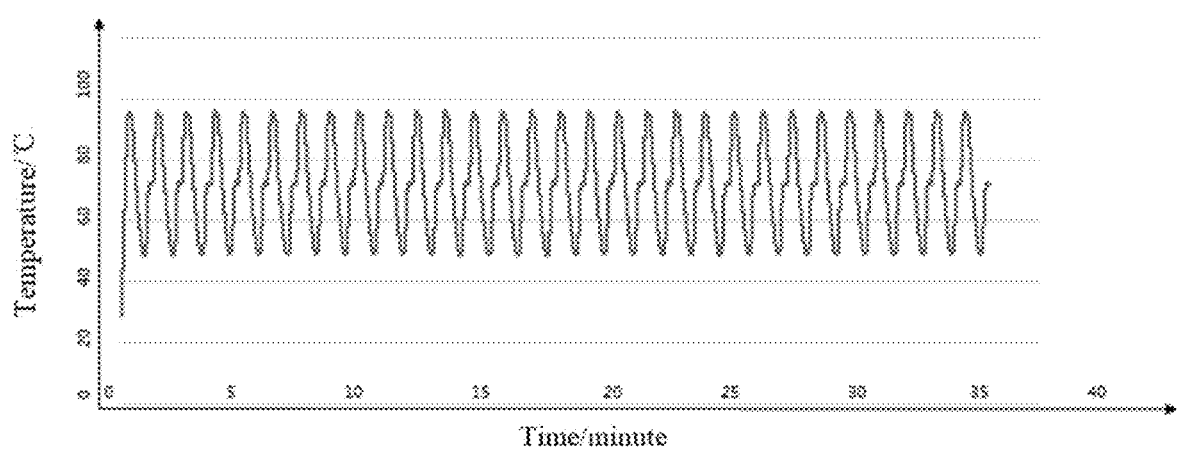
FIG. 8A is a temperature-to-time relationship curve of a reaction system during thermal cycle provided by some embodiments of the present disclosure.
Figure 8B:
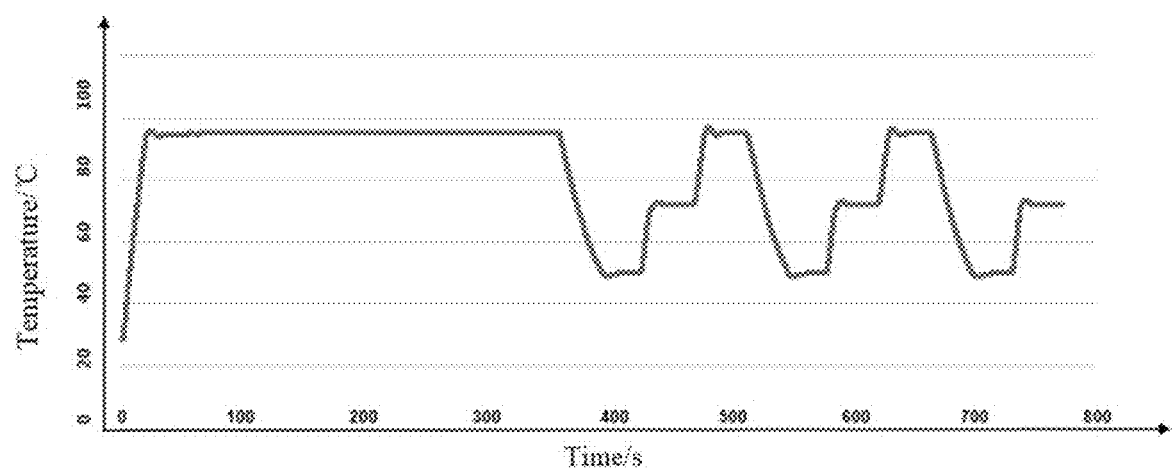
FIG. 8B is a temperature-to-time relationship curve of a reaction system during thermal cycle including a pre-denaturation process provided by some embodiments of the present disclosure.

Next, the thermal cycle amplification process is performed by using the three-step dPCR. The oil-sealed detection chip 610 is placed on a chip platform of the reaction system 600 and fixed by a clamp, so that the electrode is electrically connected to the control electrode of the detection chip 610. The parameter setting is performed by, for example, using a parameter setting button. The cycle parameters are: denaturation at 95° C. for 15 seconds, annealing at 55° C. for 45 seconds, and extending at 72° C. for 45 seconds, and a total of 30 thermal cycles are set. For example, a pre-denaturation at 95° C. for 5 minutes may also be set. The droplets, which contain the template DNA, in the micro-reaction chambers in the detection chip 610 are subjected to the PCR amplification reaction, and the droplets, which do not contain the template DNA, in the micro-reaction chambers are used as the control group. For example, the relationship curve of the temperature with respect to time of the thermal cycle is illustrated in FIG. 8A and FIG. 8B. It can be seen that the temperature control effect of the thermal cycle is good and accurate temperature control can be achieved.

Figure 8C:
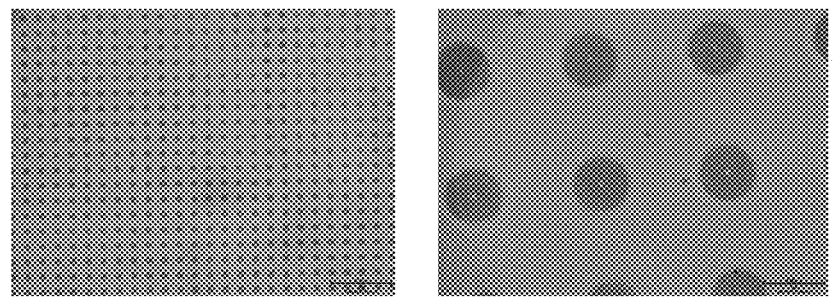
FIG. 8C is an effect diagram of a detection chip, which is provided with self-absorption liquid sample injection and oil sealing, of a reaction system provided by some embodiments of the present disclosure.

It should be noted that before performing PCR amplification, the micro-reaction chambers can be filled with bovine serum albumin (BSA) solution of 0.2% (mass fraction) and immersed for 1 hour, so as to attenuate the adsorption of the PCR reagent and sample template on the internal surface of the micro-reaction chamber and improve the reaction efficiency and detection accuracy. Then, the BSA solution is extracted by using a micro-pump, and the reaction system liquid is injected into the micro-reaction chambers and then is sealed with oil. For example, the effect diagram after self-absorption liquid sample injection and oil sealing is illustrated in FIG. 8C. For example, oil sealing can be achieved by using mineral oil, liquid paraffin, isopropyl palmitate butyl laurate, perfluoroalkane oil, etc. to seal the sample inlet and the sample outlet, thereby preventing the reaction system liquid from volatilizing.

Figure 8D:
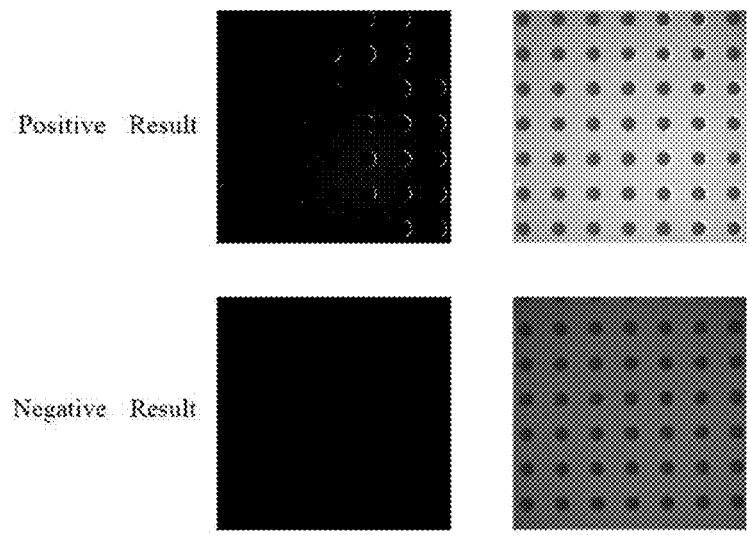
FIG. 8D is a comparison diagram of a negative result and a positive result of a gene mutation of an epidermal growth factor receptor (EGFR) of a No. 19 expressed region provided by some embodiments of the present disclosure.

After 30 cycles of amplification, the detection chip 610 is taken out and observed through a fluorescent microscope, and the excitation wavelength is 450 nm to 480 nm, thereby obtaining the positive control result and negative control result illustrated in FIG. 8D. For example, as illustrated in FIG. 8D, in the case where the reaction system liquid contains the No. 19 expressed region of the EGFR gene mutation, because the reaction system liquid includes the specific PCR amplification primers of the No. 19 expressed region of the EGFR gene mutation, the mutated No. 19 expressed region is greatly amplified under the effect of the PCR amplification primers. Therefore, the liquid to be detected appears a positive result, that is, the fluorescent reaction appears in at least some of the micro-reaction chambers. In the case where the reaction system liquid does not contain the No. 19 expressed region of the EGFR gene mutation, the liquid to be detected appears a negative result, that is, no fluorescent reaction appears in any one of the micro-reaction chambers. Thus, the detection of the No. 19 expressed region of the EGFR gene is implemented.

At least one embodiment of the present disclosure further provides a method for operating a detection chip, and the method can be used to operate the detection chip according to any one of the embodiments of the present disclosure. This method facilitates the droplet automatically entering each of the micro-reaction chambers of the detection chip, which can implement effective sample injection and avoid liquid interference, and further can effectively control the temperature of the micro-reaction chambers of the detection chip and implement the temperature cycle without performing the driving operation on the droplet or without external heating equipment, so that allow the detection chip to be with high integration, the operation is simple, and the production cost is low.

Figure 9:
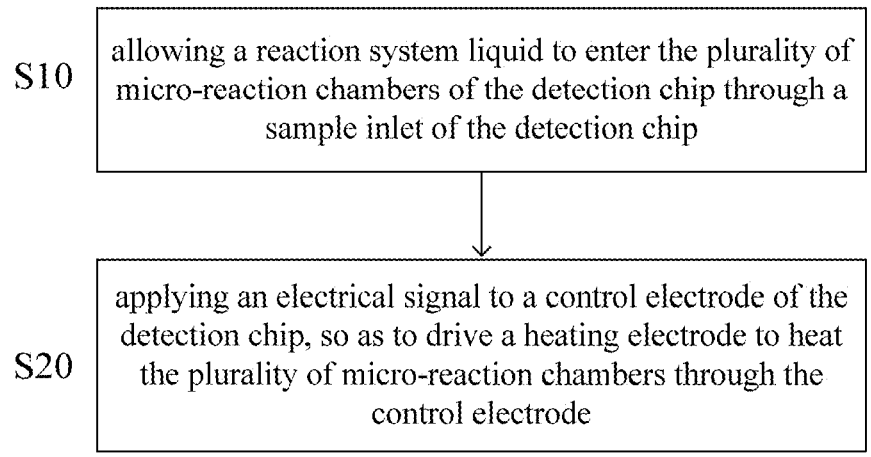
FIG. 9 is a schematic flowchart of a method for operating a detection chip provided by some embodiments of the present disclosure.

FIG. 9 is a schematic flowchart of a method for operating a detection chip provided by some embodiments of the present disclosure. For example, as illustrated in FIG. 9, the method includes following steps:

step S10: allowing a reaction system liquid to enter the plurality of micro-reaction chambers 110 of the detection chip 100 through a sample inlet 21 of the detection chip 100; and step S20: applying an electrical signal to a control electrode 15 of the detection chip 100, so as to drive a heating electrode 12 to heat the plurality of micro-reaction chambers 110 through the control electrode 15.

For example, the method further includes: cooling the plurality of micro-reaction chambers 110 to allow temperatures of the plurality of micro-reaction chambers 110 to change, so that the reaction system liquid in the plurality of micro-reaction chambers 110 is subjected to a temperature cycle comprising a denaturation phase, an annealing phase, and an extending phase. For example, the micro-reaction chambers 110 can be cooled by an air-cooled equipment with a simple structure, and the temperature cycle is easy to be implemented.

For example, the method further includes: performing an optical detection on the detection chip 100 to obtain a fluorescent image.

It should be noted that in some embodiments of the present disclosure, the method may further include more steps, which may be determined according to practical requirements, and the embodiments of the present disclosure are not limited in this aspect. The detailed descriptions and technical effects of the method can be with reference to the above descriptions of the detection chip 100 and the reaction system 600, and details are not described herein again.

Hereinafter, a method for manufacturing the detection chip 100 provided by some embodiments of the present disclosure is briefly described.

The method for manufacturing the detection chip 100 includes the following steps: forming the heating electrode 12 on the first substrate 10, and forming the micro-cavity defining layer 11 on the first substrate 10. The micro-cavity defining layer 11 defines the plurality of micro-reaction chambers 110.

For example, forming the heating electrode 12 on the first substrate 10 may include: sputtering a conductive layer (for example, an ITO layer) on a side, away from the first substrate 10, of the first insulating layer 16, and sequentially performing exposure, development, dry-etching, peeling and other processes on the conductive layer, so as to obtain the heating electrode 12.

For example, the micro-reaction chambers 110 can be directly prepared on the first substrate 10 through a semiconductor patterning process (including a photolithography process and a plasma vapor deposition process), the process is simple, large-scale mass production can be implemented, and the production cost is low.

For example, forming the micro-cavity defining layer 11 includes: depositing a defining material layer on the first substrate 10, and performing a patterning process on the defining material layer to obtain the micro-cavity defining layer 11. The defining material layer may be a photoresist layer, and performing the patterning process on the defining material layer to obtain the micro-cavity defining layer 11 includes: exposing and developing the defining material layer by using a mask, so as to form the plurality of micro-reaction chambers 110 in the defining material layer, thereby obtaining the micro-cavity defining layer 11.

For example, the method further includes: forming the hydrophilic layer 14 on a surface, away from the first substrate 10, of the micro-cavity defining layer 11, and forming the hydrophilic layer 14 on the sidewall 1101 and the bottom 1102 of each of the plurality of micro-reaction chambers 110.

Figure 10A:
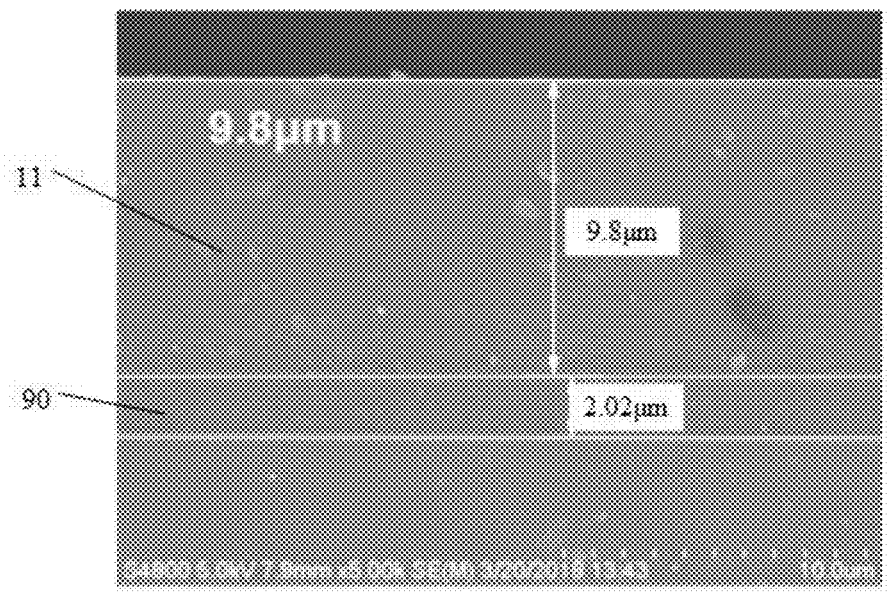
FIG. 10A is a schematic scanning electron microscope diagram of a micro-cavity defining layer of a detection chip provided by some embodiments of the present disclosure.
Figure 10B:
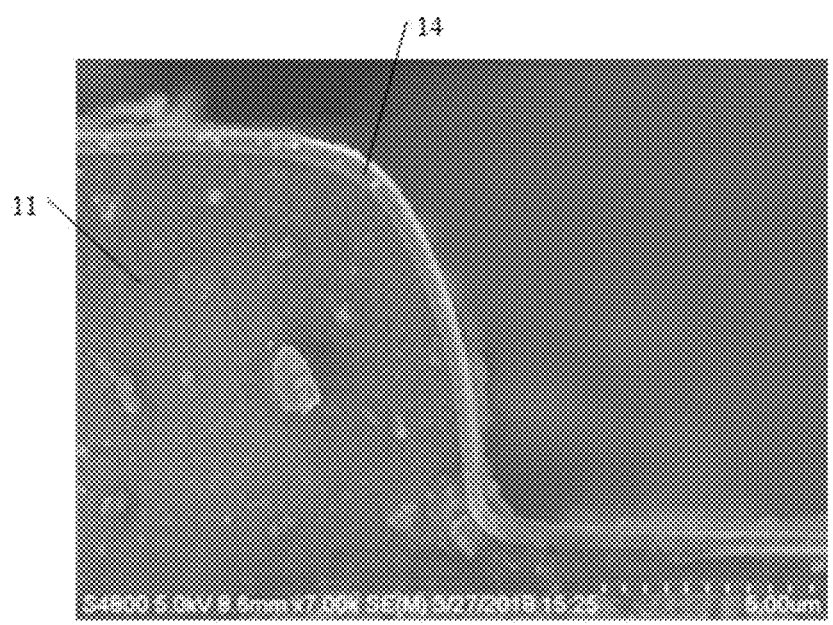
FIG. 10B is a schematic scanning electron microscope diagram of a micro-cavity defining layer and a hydrophilic layer of a detection chip provided by some embodiments of the present disclosure.

For example, in some embodiments, the process of forming the micro-cavity defining layer 11 is described as follows. First, the first substrate 10 is provided, the optical adhesive 90 (i.e., OC adhesive) is spin-coated at a speed of 1500 rpm for 45 seconds, and then the optical adhesive is cured for 30 minutes at a temperature of 230° C. On the first substrate 10 after the optical adhesive 90 is coated, a photoresist (for example, the model is KMH-T546, the thermal weight loss temperature is 320° C.) is spin-coated at a speed of 300 rpm, and the photoresist is baked for 2 minutes at a temperature of 90° C. The photoresist is repeatedly spin-coated and the above process is performed once more, so as to obtain a photoresist layer. Next, the photoresist layer is exposed through a mask to obtain a target pattern. The exposure intensity is 999 mJ, the gap value (i.e., the distance between the mask and the first substrate 10) is 100 μm, and the exposure time is 15 seconds. The developing solution is used to develop the exposed photoresist layer for 45 seconds, the developed photoresist layer is cured for 30 minutes at a temperature of 230° C., and finally, the micro-cavity defining layer 11 is obtained. As illustrated in FIG. 10A, the thickness of the optical adhesive 90 is about 2.02 μm, and the thickness of the micro-cavity defining layer 11 is about 9.8 μm. As illustrated in FIG. 10B, after the micro-cavity defining layer 11 is obtained, a silicon dioxide layer can be deposited on the micro-cavity defining layer 11 by using plasma enhanced chemical vapor deposition (PECVD) to obtain the hydrophilic layer 14. The thickness of the hydrophilic layer 14 is about 300 nm, and the hydrophilic layer 14 completely covers the surface of the micro-cavity defining layer 11.

It should be noted that prior to forming each film layer on the first substrate 10 and the second substrate 20, the first substrate 10 and the second substrate 20 may be cleaned, so as to facilitate depositing the material layer on the first substrate 10 and the second substrate 20.

For example, forming the control electrode 15 on the first substrate 10 may include: sputtering a metal conductive layer on the first substrate 10, and then sequentially performing exposure, development, etching, peeling and other processes on the metal conductive layer, so as to obtain the control electrode 15. For example, the metal conductive layer is a stack formed of molybdenum-aluminum & neodymium-molybdenum (Mo—AlNd—Mo).

For example, forming the first insulating layer 16 on the first substrate 10 includes: depositing an insulating material layer on the first substrate 10, on which the control electrode 15 is formed, by using a deposition process, and then sequentially performing exposure, development, via hole etching, peeling and other processes on the insulating material layer, so as to obtain the first insulating layer 16. For example, the via hole 160 may be formed in the first insulating layer 16.

For example, forming the second insulating layer 17 on the first substrate 10 includes: depositing an insulating layer (for example, a silicon dioxide layer and/or a silicon nitride layer) on a surface, away from the first insulating layer 16, of the heating electrode 12, so as to obtain the second insulating layer 17.

It should be noted that, in the above-mentioned method, the method for preparing the heating electrode 12, the control electrode 15, the first insulating layer 16, the second insulating layer 17, etc. may be implemented by using a semiconductor manufacturing process.

For example, forming the sample inlet 21 and the sample outlet 22 may include: first preparing the first via hole and the second via hole on the second substrate 20 by laser array punching, and then forming the third via hole and the fourth via hole in the hydrophobic layer 13 by using a patterning process. The first via hole exposes the third via hole, and the second via hole exposes the fourth via hole. The first via hole and the third via hole constitute the sample inlet 21, and the second via hole and the fourth via hole constitute the sample outlet 22.

For example, the method further includes: curing and sealing the first substrate 10 and the second substrate 20 with a frame sealant. The frame sealant includes a plurality of spacers 18, and the plurality of spacers 18 may be a shape of a sphere.

The following statements should be noted.

(1) The accompanying drawings involve only the structure(s) in connection with the embodiment(s) of the present disclosure, and other structure(s) can be referred to common design(s).

(2) In case of no conflict, features in one embodiment or in different embodiments can be combined to obtain new embodiments.

What have been described above are only specific implementations of the present disclosure, the protection scope of the present disclosure is not limited thereto, and the protection scope of the present disclosure should be based on the protection scope of the claims.

What is claimed is:

1. A detection chip, comprising:
   a first substrate;
   a micro-cavity defining layer on the first substrate and defining a plurality of micro-reaction chambers, wherein each of the plurality of micro-reaction chambers comprises a reaction trap, the reaction trap comprises a sidewall and a bottom, the micro-cavity defining layer comprises a spacing region between the plurality of micro-reaction chambers, and the spacing region comprises a first region adjacent to sidewalls of the plurality of micro-reaction chambers, and a second region non-adjacent to the sidewalls of the plurality of micro-reaction chambers;
   a hydrophilic layer covering the sidewall and the bottom of each of the plurality of micro-reaction chambers; and a hydrophobic layer covering the second region in the spacing region of the micro-cavity defining layer, wherein the hydrophilic layer further covers the first region and the second region in the spacing region of the micro-cavity defining layer, and the hydrophobic layer only covers the hydrophilic layer in the second region excluding the first region, so that the micro-cavity defining layer in the second region is covered by the hydrophilic layer and the hydrophobic layer which are stacked, wherein the detection chip further comprises a control electrode, the control electrode is on the first substrate and is electrically connected to the heating electrode through a via hole or overlapped with the heating electrode, and the control electrode is configured to apply an electrical signal to the heating electrode.

2. The detection chip according to claim 1, wherein the first region is in a circular ring shape, and a width of the circular ring shape is 2 μm to 5 μm.

3. The detection chip according to claim 1, further comprising a heating electrode, wherein the heating electrode is on the first substrate and closer to the first substrate than the micro-cavity defining layer, and is configured to heat the plurality of micro-reaction chambers, and orthographic projections of the plurality of micro-reaction chambers on the first substrate are within an orthographic projection of the heating electrode on the first substrate.

4. The detection chip according to claim 1, wherein the plurality of micro-reaction chambers are arranged in an array on the first substrate.

5. The detection chip according to claim 3, further comprising a second substrate, wherein the second substrate is opposite to the first substrate, the hydrophobic layer further covers a side, facing the first substrate, of the second substrate, and the micro-cavity defining layer is on a side, facing the second substrate, of the first substrate.

6. The detection chip according to claim 5, further comprising a control electrode, wherein the control electrode is on the first substrate and is electrically connected to the heating electrode through a via hole or overlapped with the heating electrode, and the control electrode is configured to apply an electrical signal to the heating electrode.

7. The detection chip according to claim 6, further comprising a first insulating layer, wherein the first insulating layer covers the control electrode, and the heating electrode is on the first insulating layer; and the first insulating layer comprises the via hole penetrating the first insulating layer, and the heating electrode is electrically connected to the control electrode through the via hole.

8. The detection chip according to claim 3, further comprising a second insulating layer, wherein the second insulating layer is between the heating electrode and the micro-cavity defining layer.

9. The detection chip according to claim 7, wherein the first substrate comprises a reaction region and a peripheral region, the peripheral region is at least partially around the reaction region, the reaction region comprises a functional region, the micro-cavity defining layer is in the functional region, the control electrode and the via hole are in the peripheral region, and the heating electrode is in the reaction region and the peripheral region.

10. The detection chip according to claim 9, wherein the via hole comprises a first via hole group and a second via hole group, and the first via hole group and the second via hole group are on two opposite sides of the peripheral region, respectively;

the control electrode comprises a first control electrode group and a second control electrode group;

the first control electrode group is on a same side as the first via hole group in the peripheral region, and is electrically connected to the heating electrode through the first via hole group; and the second control electrode group extends along the peripheral region and is partially around the heating electrode, and the second control electrode group is electrically connected to the heating electrode through the second via hole group.

11. The detection chip according to claim 9, further comprising a plurality of spacers, wherein the plurality of spacers are in the peripheral region and between the first substrate and the second substrate, and the plurality of spacers are configured to maintain a distance between the first substrate and the second substrate.

12. The detection chip according to claim 11, wherein a height of the spacers is greater than a height of the micro-cavity defining layer in a direction perpendicular to the first substrate.

13. The detection chip according to claim 9, further comprising a sample inlet and a sample outlet, wherein the reaction region further comprises a non-functional region, the sample inlet and the sample outlet are both in the non-functional region and on different sides of the functional region, and both the sample inlet and the sample outlet penetrate the second substrate and the hydrophobic layer covering the second substrate.

14. The detection chip according to claim 13, wherein the sample inlet and the sample outlet are in the non-functional region and are symmetrically distributed on different sides of the functional region.

15. The detection chip according to claim 9, further comprising a first temperature sensor, wherein the first temperature sensor is on a side, away from the micro-cavity defining layer, of the first substrate, and the first temperature sensor is in the reaction region and configured to detect a temperature of the reaction region.

16. A reaction system, comprising a control device and the detection chip according to claim 1, wherein the control device is electrically connected to the detection chip, and is configured to apply an electrical signal to the detection chip to drive a heating electrode of the detection chip.

17. The reaction system according to claim 16, further comprising a second temperature sensor, wherein the second temperature sensor is on a side, away from the micro-cavity defining layer, of the first substrate of the detection chip, the second temperature sensor is in a reaction region of the first substrate, and the second temperature sensor is configured to detect a temperature of the reaction region of the detection chip.

18. A reaction system, comprising a control device and the detection chip according to claim 15,
wherein the control device is electrically connected to the detection chip, and is configured to apply an electrical signal to the detection chip to drive the heating electrode of the detection chip.

19. A method for operating the detection chip according to claim 1, comprising:
allowing a reaction system liquid to enter the plurality of micro-reaction chambers of the detection chip through a sample inlet of the detection chip; and
applying an electrical signal to a control electrode of the detection chip, so as to drive a heating electrode of the detection chip to heat the plurality of micro-reaction chambers through the control electrode.

* * * * *

UNITED STATES PATENT AND TRADEMARK OFFICE
CERTIFICATE OF CORRECTION

| | |
|---|---|
| PATENT NO. | : 11,654,435 B2 |
| APPLICATION NO. | : 16/753115 |
| DATED | : May 23, 2023 |
| INVENTOR(S) | : Zijian Zhao, Siyi Yin and Yudan Yin |

It is certified that error appears in the above-identified patent and that said Letters Patent is hereby corrected as shown below:

On the Title Page

Item (73) Assignees should read: BEIJING BOE TECHNOLOGY DEVELOPMENT CO., LTD., Beijing (CN); BOE TECHNOLOGY GROUP CO., LTD., Beijing (CN)

Signed and Sealed this
Twenty-fourth Day of September, 2024

Katherine Kelly Vidal
*Director of the United States Patent and Trademark Office*